US008790891B2

(12) United States Patent
Irimia

(10) Patent No.: US 8,790,891 B2
(45) Date of Patent: Jul. 29, 2014

(54) MICROFLUIDIC CELL MOTILITY ASSAY

(75) Inventor: Daniel Irimia, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 144 days.

(21) Appl. No.: 13/257,464

(22) PCT Filed: Mar. 19, 2010

(86) PCT No.: PCT/US2010/027980
§ 371 (c)(1),
(2), (4) Date: Dec. 1, 2011

(87) PCT Pub. No.: WO2010/108095
PCT Pub. Date: Sep. 23, 2010

(65) Prior Publication Data

US 2012/0094325 A1 Apr. 19, 2012

Related U.S. Application Data

(60) Provisional application No. 61/161,764, filed on Mar. 19, 2009.

(51) Int. Cl.
*C12Q 1/04* (2006.01)
*C12Q 1/02* (2006.01)

(52) U.S. Cl.
USPC ............................................ 435/34; 435/29

(58) Field of Classification Search
USPC ................................................... 435/34, 29
See application file for complete search history.

(56) References Cited

U.S. PATENT DOCUMENTS

| | | | | |
|---|---|---|---|---|
| 5,744,366 | A | 4/1998 | Kricka et al. | |
| 6,811,968 | B2 * | 11/2004 | Kirk et al. | 435/4 |
| 6,921,660 | B2 | 7/2005 | Kirk et al. | |
| 7,326,563 | B2 | 2/2008 | Kim et al. | |
| 7,374,906 | B2 | 5/2008 | Kirk et al. | |
| 2005/0271548 | A1 | 12/2005 | Yang et al. | |
| 2011/0117579 | A1 | 5/2011 | Irimia | |

FOREIGN PATENT DOCUMENTS

| | | |
|---|---|---|
| WO | WO 02/44730 | 6/2002 |
| WO | WO 2009/102453 | 8/2009 |
| WO | 2010/108095 | 9/2010 |

OTHER PUBLICATIONS

International Search Report and Written Opinion dated Oct. 26, 2010 issued in International application No. PCT/US2010/027980.

Albini and Benelli "The chemoinvasion assay: a method to assess tumor and endothelial cell invasion and its modulation" Nat Protoc. 2(3):504-511 (2007).

Beningo et al. "Responses of fibroblasts to anchorage of dorsal extracellular matrix receptors" Proc Natl Acad Sci USA 101(52):18024-18029 (2004).

Bovin and Gabius "Polymer-immobilized carbohydrate ligands: Versatile Chemical Tools for Biochemistry and Medical Sciences" Chemical Society Reviews 24(6):413-421 (1995).

Boyden "The Chemotactic Effect of Mixtures of Antibody and Antigen on Polymorphonuclear Leucocytes" Journal of Experimental Medicine 115 (3):453-466 (1962).

Brandley and Schnaar "Cell-Surface Carbohydrates in Cell Recognition and Response" Journal of Leukocyte Biology 40:97-111 (1986).

Carmignani et al. "Intraperitoneal cancer dissemination: Mechanisms of the patterns of spread" Cancer Metastasis Rev. 22:465-472 (2003).

Cavallaro and Christofori "Cell adhesion and signalling by cadherins and Ig-CAMs in cancer" Nature Reviews Cancer 4:118-132 (2004).

Chiang and Massague "Molecular Basis of Metastasis" N Engl J Med. 359 (26):2814-2823 (2008).

Condeelis and Segall "Intravital imaging of cell movement in tumours" Nature Reviews Cancer 3:921-930 (2003).

Decaestecker et al. "Can anti-migratory drugs be screened in vitro? A review of 2D and 3D assays for the quantitative analysis of cell migration" Medicinal Research Reviews 27(2):149-176 (2007).

Demou and McIntire "Fully automated three-dimensional tracking of cancer cells in collagen gels: Determination of motility phenotypes at the cellular level" Cancer Research 62(18):5301-5307 (2002).

Even-Ram and Yamada "Cell migration in 3D matrix" Current Opinion in Cell Biology 17:524-532 (2005).

Feki et al. "Dissemination of intraperitoneal ovarian cancer: Discussion of mechanisms and demonstration of lymphatic spreading in ovarian cancer model" Crit Rev Oncol Hematol. 72:1-9 (2009).

Friedl and Wolf "Tumour-cell invasion and migration: Diversity and escape mechanisms" Nature Reviews Cancer 3:362-374 (2003).

Gerhardt and Semb "Pericytes: gatekeepers in tumour cell metastasis?" J Mol Med 86:135-144 (2008).

Giese and Westphal "Glioma invasion in the central nervous system" Neurosurgery 39(2):235-252 (1996).

Hanahan and Weinberg "The Hallmarks of Cancer" Cell 100:57-70 (2000).

Irimia et al. "Adaptive-Control Model for Neutrophil Orientation in the Direction of Chemical Gradients" Biophysical Journal 96:3897-3916 (2009).

Irimia et al. "Polar stimulation and constrained cell migration in microfluidic channels" Lab Chip 7:1783-1790 (2007).

Irimia et al. "Microfluidic system for measuring neutrophil migratory responses to fast switches of chemical gradients" Lab Chip 6:191-198 (2006).

Irimia et al. "Universal Microfluidic Gradient Generator" Analytical Chemistry 78(10):3472-3477 (2006).

Keenan and Folch, "Biomolecular gradients in cell culture systems" Lab Chip 8:34-57 (2008).

(Continued)

*Primary Examiner* — Karen Cochrane Carlson
*Assistant Examiner* — Natalie Moss
(74) *Attorney, Agent, or Firm* — Fish & Richardson P.C.

(57) ABSTRACT

Certain isolated motile cells spontaneously migrate unidirectionally through a mechanically confined space, such as a microcapillary channel, in the absence of an external gradient (e.g., a chemical gradient). Assays and methods for detecting motile cells, and identifying chemical agents that inhibit cell migration, can include detecting the movement of motile cancer cells through a microcapillary channel.

18 Claims, 16 Drawing Sheets

(56) References Cited

OTHER PUBLICATIONS

Keenan et al. "Microfluidic 'jets' for generating steady-state gradients of soluble molecules on open surfaces" Applied Physics Letters 89:114103 (2006) (3 pages).
Kuntz and Saltzman, "Neutrophil Motility in Extracellular Matrix Gels: Mesh Size and Adhesion Affect Speed of Migration" Biophysical Journal 72:1472-1480 (1997).
Lammermann et al. "Rapid leukocyte migration by integrin-independent flowing and squeezing" Nature 453:51-55 (2008).
Lee et al. "Three-dimensional micropatterning of bioactive hydrogels via two-photon laser scanning photolithography for guided 3D cell migration" Biomaterials 29:2962-2968 (2008).
Levy et al. "Endoscopic ultrasound fine-needle aspiration detection of extravascular migratory metastasis from a remotely located pancreatic cancer" Clin Gastroenterol Hepatol. 7:246-248 (2009).
Lugassy and Barnhill "Angiotropic melanoma and extravascular migratory metastasis: A review" Adv Anal Pathol. 14:195-201 (2007).
Malawista et al. "Random locomotion and chemotaxis of human blood polymorphonuclear leukocytes from a patient with leukocyte adhesion deficiency-1: Normal displacement in close quarters via chimneying" Cell Motil. Cytoskeleton 46:183-189 (2000).
Overall and Lopez-Otin "Strategies for MMP inhibition in cancer. Innovations for the post-trial era" Nat Rev Cancer 2:657-672 (2002).
Raeber et al. "Molecularly engineered PEG hydrogels: a novel model system for proteolytically mediated cell migration" Biophysical Journal 89:1374-1388 (2005).
Rhee et al. "Microtubule function in fibroblast spreading is modulated according to the tension state of cell-matrix interactions" Proc Natl Acad Sci USA 104(13):5425-5430 (2007).
Sahai "Illuminating the metastatic process" Nature Reviews Cancer 7:737-749 (2007).
Sahai and Marshall "Differing modes of tumour cell invasion have distinct requirements for Rho/ROCK signalling and extracellular proteolysis" Nat Cell Biol. 5(8):711-719 (2003).
Sahai et al. "Simultaneous imaging of GFP, CFP and collagen in tumors in vivo using multiphoton microscopy" BMC Biotechnology 5(14):1-9 (2005).
Savage et al. "Why does cytotoxic chemotherapy cure only some cancers?" Nat Clin Pract Oncol. 6:43-52 (2009).
Sporn "The war on cancer" Lancet. 347:1377-1381 (1996).
Sugarbaker et al. "Gastrectomy, peritonectomy, and perioperative intraperitoneal chemotherapy: The evolution of treatment strategies for advanced gastric cancer" Semin Surg Oncol. 21:233-248 (2003).
Tan et al. "Mechanisms of transcoelomic metastasis in ovarian cancer" Lancet Oncol. 7:925-934 (2006).
Tanos and Rodriguez-Boulan "The epithelial polarity program: machineries involved and their hijacking by cancer" Oncogene 27:6939-6957 (2008).
Todaro et al. "Initiation of Cell Division in a Contact- Inhibited Mammalian Cell Line" J. Cell and Comp. Physiol. 66:325-333 (1965).
Vermeer et al. "Segregation of receptor and ligand regulates activation of epithelial growth factor receptor" Nature 422:322-326 (2003).
Wang et al. "Reciprocal interactions between beta1-integrin and epidermal growth factor receptor in three-dimensional basement membrane breast cultures: a different perspective in epithelial biology" Proc Natl Acad Sci USA. 95:14821-14826 (1998).
Yamada and Cukierman "Modeling tissue morphogenesis and cancer in 3D" Cell 130:601-610 (2007).
Yarrow et al. "A high-throughput cell migration assay using scratch wound healing, a comparison of image-based readout methods" BMC Biotechnology 4(21):1-9 (2004).
Zahm et al. "Cell migration and proliferation during the in vitro wound repair of the respiratory epithelium" Cell Motil. Cytoskeleton 37:33-43 (1997).
International Preliminary Report on Patentability dated Sep. 29, 2011 issued in International application No. PCT/US2010/027980.
International Search Report and Written Opinion dated Sep. 28, 2009 from International application No. PCT/US2009/000890.

* cited by examiner

| | | A | B | C | D |
|---|---|---|---|---|---|
| | Channel Size | 6 x 10μm | 20 x 10μm | 20 x 10μm | 20 x 10μm |
| | Protein Coating | Collagen | Collagen | Collagen | Fibronectin |
| * | Cell Release | EDTA | EDTA | Trypsin | Trypsin |

MICROFLUIDIC CELL MOTILITY ASSAY

CLAIM OF PRIORITY

This application is a 371 application of International Application No. PCT/US2010/027980, filed on Mar. 19, 2010, and claims the benefit of U.S. Provisional Patent 61/161,764, filed on Mar. 19, 2009, the entire contents of which are incorporated herein by reference.

STATEMENT AS TO FEDERALLY SPONSORED RESEARCH

This invention was made with Government support under Grant No(s). CA135601 & EB002503 awarded by the National Institutes of Health. The Government has certain rights in this invention.

TECHNICAL FIELD

This disclosure relates to the detection and isolation of migratory cancer cells, and mediating cancer cell migration.

BACKGROUND

Cancer cells can migrate from a primary tumor site in a body into proximal and distant tissues where they can form metastases. The migration of the cancer cells can occur along preexisting paths in the body, such as blood or lymphatic vessels, collagen fibers, white matter tracts, or vessels for peritoneal fluid flow. Observing and quantifying the cancer cell migration processes in vivo is difficult, in part due to the natural variability and complexity of the microenvironment experienced by the moving cells and by the close interaction with other cells.

One difficulty in studying cancer cell migration is the variety of the processes involved in cell migration. Cancer cell migration is the cumulative outcome of at least four basic cellular processes that include cellular motility, invasion of the extracellular matrix (ECM), adhesion to substrates, and cell-cell communication. In addition, very low numbers of cancer cells are typically recovered from patients (e.g, a few hundred cells). Method and assays for identifying motile cancer cells in a small cancer cell population (e.g., fewer than about $10^3$ cells) can be useful, for example, in identifying potentially migratory metastatic cancer cell populations. In addition, such methods and assays can be useful to identify chemical agents that inhibit the migration of cancer cells.

SUMMARY

The present invention relates to assays and methods for detecting motile cells (e.g., cancer cells, stem cells, and fibroblasts), and identifying chemical agents that inhibit cancer cell migration. The disclosure is based in part on the surprising discovery that certain isolated cells can spontaneously migrate unidirectionally through a mechanically confined space, such as a microcapillary channel, in the absence of an external gradient (e.g., a chemical gradient). For example, cells from various metastatic tumor cell lines moved spontaneously and substantially continuously in the absence of a chemical gradient in one direction along a collagen-lined microcapillary channel having a cross-sectional area smaller than the cells outside the microcapillary channel for periods of from 3 to 72 hours. The movement of individual isolated motile cells in microcapillary channels can be quantitatively evaluated using the methods and microcapillary assay devices described herein, allowing, for example, the identification of motile cancer cells in a cancer cell population.

Significantly, motile cells passing through microcapillary channels can be isolated after passing through the microcapillary channel, permitting isolation of viable motile cells from a cancer cell population for further observation, testing and analysis. The motile cancer cells isolated by passage through a microcapillary channel were observed to have cell motility properties outside of the microcapillary (e.g., a "random walk" movement when unrestrained on a flat surface permitting two-dimensional movement) that are indistinguishable from non-motile cancer cells.

The motility of individually isolated, mechanically constrained cancer cells can be observed in a microcapillary channel by: (a) isolating a cancer cell population from a test tissue sample obtained from a patient, the cancer cell population comprising isolated cancer cells with a maximum cell diameter; (b) allowing a cancer cell from the isolated cancer cell population to enter an opening in a microcapillary channel under conditions effective to permit a single cancer cell from the cancer cell test population to enter the microcapillary channel; and (c) detecting the presence of a motile cancer cell in the cancer cell test population by observing the unidirectional movement of the cancer cell away from the opening in the microcapillary channel in the absence of a chemoattractant gradient. The microcapillary channel opening is configured to mechanically constrain the cancer cell moving along the channel, for example by having a cross sectional area that is smaller than the maximum cancer cell diameter.

Movement of cancer cells from a test population can be detected in a microcapillary channel as part of a method of detecting the presence of motile cancer cells in a test tissue sample, measuring the cell motility of a cancer cell along a length of a microcapillary channel, or identifying a metastatic cancer cell population based on detection of motile cancer cells within the microcapillary channel.

Agents that mediate cancer cell motility can also be identified by observing cancer cell motility in a mechanically confined space. For example, an isolated cancer cell test population can be contacted with a chemical agent prior to, during or after observing the cell in a mechanically constraining microcapillary channel to determine whether the chemical agent reduces the unidirectional movement of the cancer cell in the absence of a chemoattractant gradient within the microcapillary channel after contacting the cancer cell with the chemical agent. Accordingly, methods of identifying chemical agents that inhibit, permit or even promote cancer cell motility can be identified.

Systems for monitoring the motility of cancer cells in the absence of a chemoattractant gradient can include an enclosed microcapillary with a cell contact surface (e.g., collagen) defining a microcapillary channel and a detector adapted to detect the position and movement of a cell within the microcapillary channel. The microcapillary channel can be configured to mechanically confine a cell within the channel. For example, the microcapillary channel can have an opening adapted to receive a single cell from a reservoir and have at least one side with a length of up to 20 micrometers measured perpendicular to the length of the microcapillary channel. The microcapillary channel can (i) extend along a length from the opening to a distal end, and having a substantially constant cross-sectional area, (ii) have at least one side with a length of 10-15 micrometers measured perpendicular to the length of the microcapillary channel, (iii) have a ratio between the cross-sectional area of the microcapillary channel and the length of the microcapillary channel of less than 1.0 micrometer and/or (iv) have an optically transparent portion. The detector can be, for example, an optical microscope positioned to observe a cell within the transparent portion of the microcapillary channel.

In some examples, the system can be a microcapillary array including a plurality of microcapillary channels extending from a reservoir adapted to contain a cell suspension in fluid communication with the openings of the plurality of microcapillary channels. The system can also include a fluid medium container in fluid communication with the distal ends of the plurality of microcapillary arrays, and adapted to maintain the opening of the microcapillary channel in fluid communication with the distal end without creating a pressure differential across the microcapillary channel.

The systems and methods described in this disclosure can provide one or more of the following advantages.

The systems and methods can provide improved quantification of cell migration characteristics. For example, these systems and methods can provide comprehensive information including, for example, the average velocity of migration/invasion, the distribution of velocities in the population with single cell resolution, and information regarding cell morphology during migration in contrast to the single number result provided by earlier approaches. Moreover; these systems and methods are compatible with single cell fluorescent imaging.

These systems and methods can provide an improved ability to visualize cells during migration relative to end point assay in which it is not possible to image the cells during migration. For example, these systems and methods allow real time imaging of migrating cells and are compatible with many imaging techniques (e.g., brightfield, phase, fluorescence, etc). These systems and methods can provide single-cell resolution which is very useful feature, for example, in studying cancer cells migration and metastasis. These systems and methods can also provide quantitative measurement of cell invasion through different gels at single-cell resolution.

These systems and methods can provide highly efficient, fast analyses from small samples. The required sample size can be as small as less than 100 cells/condition in contrast to the much larger sample sizes (e.g., 1 million+cells/condition) for other approaches. These systems and methods can provide first results as quickly as few hours in contrast to prior approaches which typically require at least 24 hours. Moreover, additional processing of the cells can be performed during/after assay without cell labeling.

These systems and methods can provide controls for migration experiments in part through flexibility that allows direct comparison between different cell types. Moreover, these systems and methods can provide results independent of cell growth and division thus avoiding the confounding effect of cell multiplication during the assay.

The details of one or more embodiments are set forth in the accompanying drawings and the description below. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. Other features, objects, and advantages will be apparent from the description, drawings, and from the claims.

DESCRIPTION OF DRAWINGS

FIG. 7A is an optical micrograph of a portion of the fifth microfluidic device; FIG. 7B is a schematic side view of the fifth microfluidic device.

Unless otherwise indicated, like reference symbols in the various drawings indicate like elements.

DETAILED DESCRIPTION

Figure 1A:
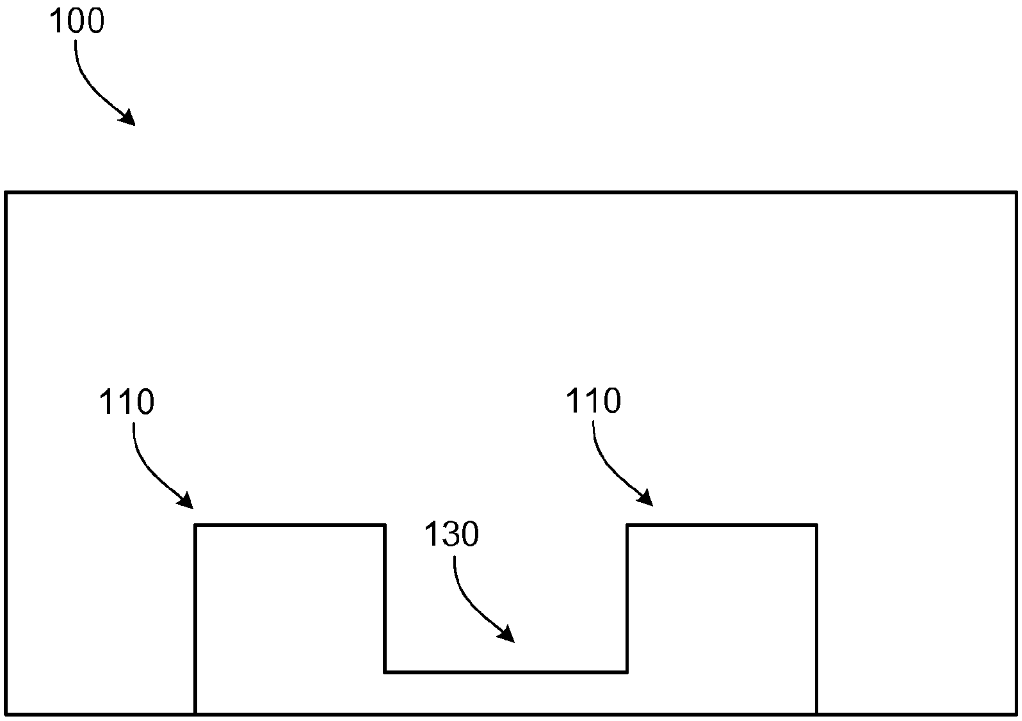
FIGS. 1A-1B are schematic representations of a first microfluidic device.
Figure 1B:
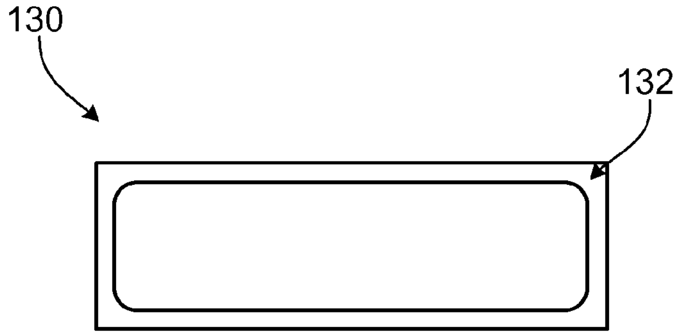

Referring now to FIGS. 1A-1B, the migration of mechanically-constrained isolated cancer cells can be observed within a microfluidic device 100 containing one or more microcapillaries 130. FIG. 1B shows a cross-sectional view of the microcapillary 130 shown in FIG. 1A. Each microcapillary 130 can extend from an opening adapted to receive a single cell, and can have an interior surface defining a microcapillary channel. In the first microfluidic device 100, the microcapillary 130 extends along a length to a distal end, with the opening and the distal end in fluid communication with separate microwells.

The size and configuration of the cross-sectional area of the microcapillary can be selected to permit movement of a cancer cell along the length of the microcapillary 130 by mechanically constraining the cancer cell. Preferably, the microcapillary 130 encloses a microcapillary channel configured to contact the cell on at least three sides. The microcapillary 130 has a cross-sectional configuration selected to mechanically constrain a cell within the microcapillary in at least one dimension. As used herein, to "mechanically constrain" a cell refers to placement of the cell within a space having at least one dimension that is smaller than the maximum diameter of the unconstrained cell in a cell media. Preferably, the cell is constrained within a channel constraining cell movement to one dimension. For example, the microcapillary 130 can be configured to contact the cell on at least three sides (e.g., with a rectangular cross-section) or on all sides (e.g., with a circular cross-section). The cross-sectional area of the microcapillary 130 and/or the microcapillary channel (e.g., width×height for a rectangular cross-sectional geometry) can be less than the maximum diameter of a cell in a microwell 110, outside the microcapillary. For example, to observe movement of cancer cells with a maximum unconstrained diameter of about 15-20 micrometers along the microcapillary 130, the microcapillary 130 can define a microcapillary channel with a rectangular cross section having at least one dimension less than about 15 micrometers (e.g., about 2 micrometers to about 10-15 micrometers along one dimension of length, width or diameter by at least about 50 micrometers in length).

In some preferred embodiments, the dimensions/ratios of dimensions for the capillaries are chosen such that the cross sectional area of the capillaries are smaller than the cross section area of the cells (either when in suspension, or when attached) to be tested. For example, for cells of 15 μm diameter (180 $\mu m^2$ cross section when in suspension), an optimal size of the channels where the persistent motility occurs is about 10×10μm. In the case of 10 μm diameter cells, a channel that is 8×8 μm or smaller would be better suited. Sizing of the capillaries should also reflect that some cells, when attached to a surface, stretch a lot and thus reduce their cross sectional area. In this respect, a ratio of 0.5 or smaller between the cross section of the cells in suspension and the cross section of the channel is expected to work well.

In one particular example, a microcapillary channel can have a rectangular cross section about 5 micrometers by 50 micrometers and a length of about 650 micrometers. Accordingly, the ratio of the cross-sectional area (250 square micrometers) to the length of the microcapillary channel is about 0.38 micrometer (250 square micrometers/650 micrometers). The ratio of the cross-sectional area to the length of the microcapillary channel is preferably less than 1.0 (e.g., less than about 0.5). The speed and persistence of migration for cells in the microcapillaries 130 may be significantly higher than for cells on flat surfaces. Preferably, the microcapillary 130 and/or microcapillary channel has a substantially uniform cross-sectional area along the length of the microcapillary. Because cell motility within the microcapillary 130 is restricted only along the capillary, in one linear dimension, the motility is easy to image and easy to quantify for extended periods of times. We have tracked cells for more than 72 hours. For capillaries with side channels, loops or other geometries the motility can also be quantified.

The interior surface of the microcapillary 130 can be coated with a cell-contact material that permits movement of a living cell along the microcapillary channel. For example, the cell-contact material can be an extracellular matrix material, such as a collagen (e.g., collagen IV, or a protein mixture). Another cell-contact material includes a gelatinous protein mixture secreted by mouse tumor cells sold under the tradename MATRIGEL by BD Biosciences. Low density matrixes (e.g. Matrigel 1:10), below what one could do with current methods, could be loaded inside the channels.

The microcapillary channel can be configured to allow cells in the capillaries to interact with matrix proteins on all sides, so that the capillary simulates a 3D environment for the cell. Motility along the capillary is however not restricted by the matrix, and consequently the device can decouple cell motility in 3D from matrix invasion. Alternatively, the microcapillary 130 can be filled with a porous cell-contact material through which cells can migrate along the length of the microcapillary 130. In some embodiments, the capillaries can be filled with an extracellular matrix protein (e.g., growth factors), in which case the ability of the cell to degrade and invade matrix is also tested. The microcapillary 130 can be coated with a cell-contact material by contacting an interior surface of the microcapillary channel with an extracellular matrix protein prior to allowing the cancer cell from the cancer cell population to enter the opening in the the microcapillary channel. The microfluidic device 100, including the portions defining the microcapillary 130, can be formed from a material that does not react with the cells being studied within the microcapillary 130. For example, the microfluidic device can be formed from a polymer such as polydimethyl siloxane (PDMS, Dow Corning, Midland. Mich.).

Figure 2:
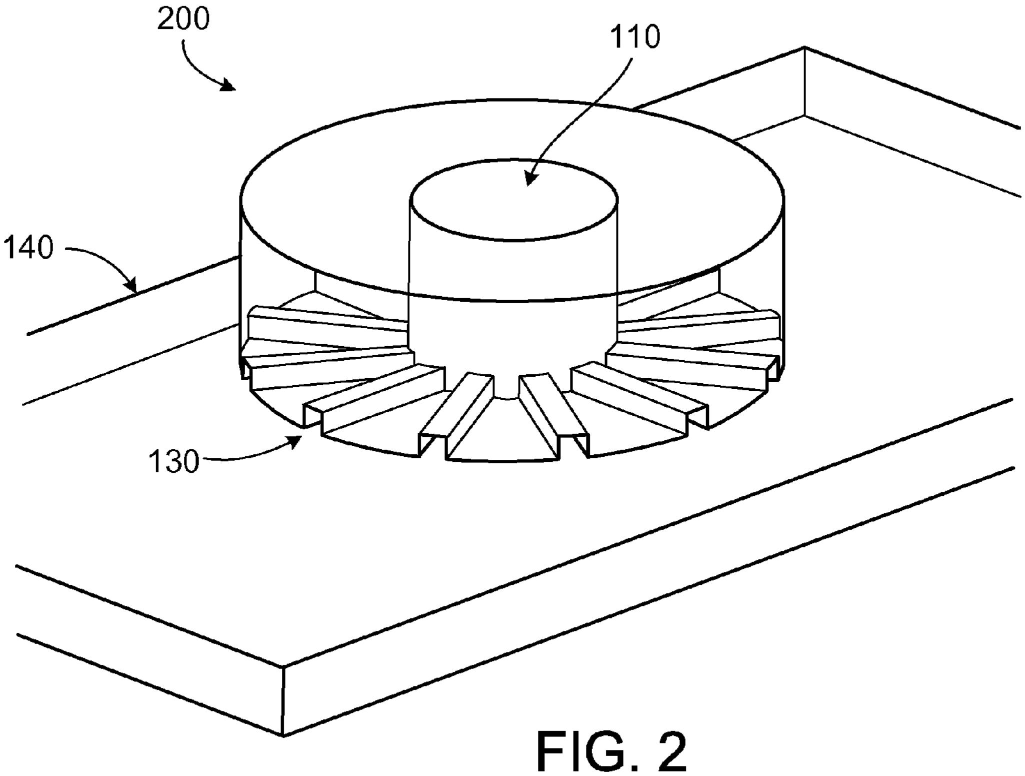
FIG. 2 is a perspective view of a second microfluidic device, including a radial array of microcapillaries.
Figure 3:
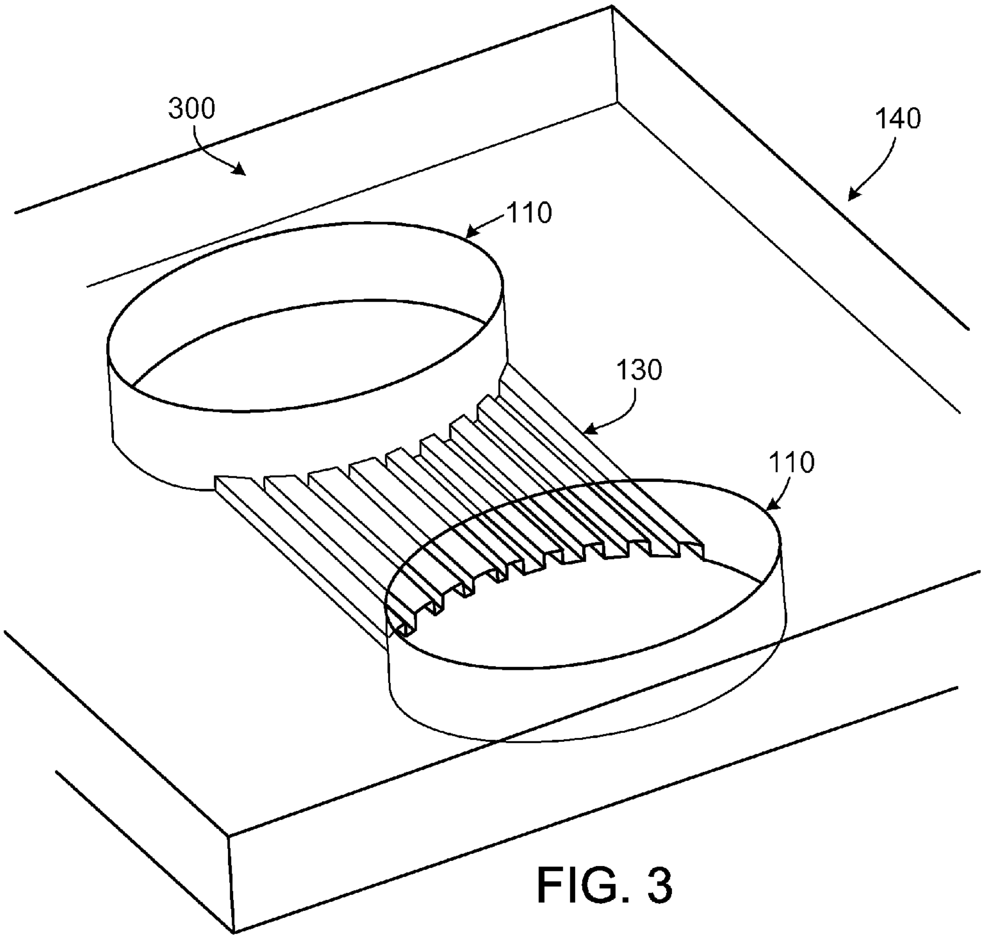
FIG. 3 is a perspective view of a third microfluidic device, including a parallel array of microcapillaries.

The microcapillary can be formed of one or more materials permitting detection of cell movement within the microcapillary channel. For example, the microcapillary can be formed of an optically transparent material. Referring now to FIG. 2, a second microfluidic device 200 can include the microwell 110 and one or more of the microcapillaries 130 that extend radially from the microwell 110. This structure can be bonded to a glass slide 140, forming the bottom wall of the microfluidic device 200. The microfluidic device 200 includes of a radial array of microcapillaries 130 of sizes comparable to cell size (2 to 20 μm), connecting one central well where cells are seeded to a larger chamber in a multi-well plate. In operation, the entire device is covered with fluid, and no pressure differential across the microcapillaries 130 exists. Cell motility is restricted to one dimension, along the microcapillaries 130. A glass slide forms the bottom of the microcapillaries 130. Cells can be seeded in the "cell wheel" as cell suspension, but after 5 minutes the cells attach and start moving on the extracellular matrix protein-coated glass surface Referring now to FIG. 3, a third microfluidic device 300 can include two microwells 110 and a parallel array of the microcapillaries 130 that extend between the two microwells 110, fluidly connecting the interiors of the microwells 110. As with the microfluidic device 200, the bottom wall of the microfluidic device 300 can be formed by a glass slide 140 bonded to the microwells 110 and microcapillaries 130.

In operation, a suspension of cancer cells can be isolated from a cancer cell population obtained from a patient can be introduced to a microwell 110 in fluid communication with the opening 112 of the microcapillary 130. Cancer cells can be introduced to the microwell 110 as a cell suspension in media. For example, isolated cancer cells can be cultured, washed with a suitable buffer (e.g., PBS) and isolated in a suitable concentration (e.g., using trypsin or 10 mM calcium chelater solution in buffer, suspending in media, centrifuged and re-suspended). Concentrations of about $10^6$ cells/mL are suitable. In this manner, the cancer cells in the suspension can be allowed to enter the opening 112 in the microcapillary 130 and enter the microcapillary channel.

The movement of motile cancer cells within the microcapillary 130 can be observed in the absence of an applied gradient. As used herein, the term "motile cancer cells" refers to cancer cells that move through a microcapillary 130 when mechanically constrained in the absence of an applied gradient. The applied gradient can be a condition that induces movement of non-motile cancer cells through the microcapillary 130, such as a chemoattractant.

Figure 4:
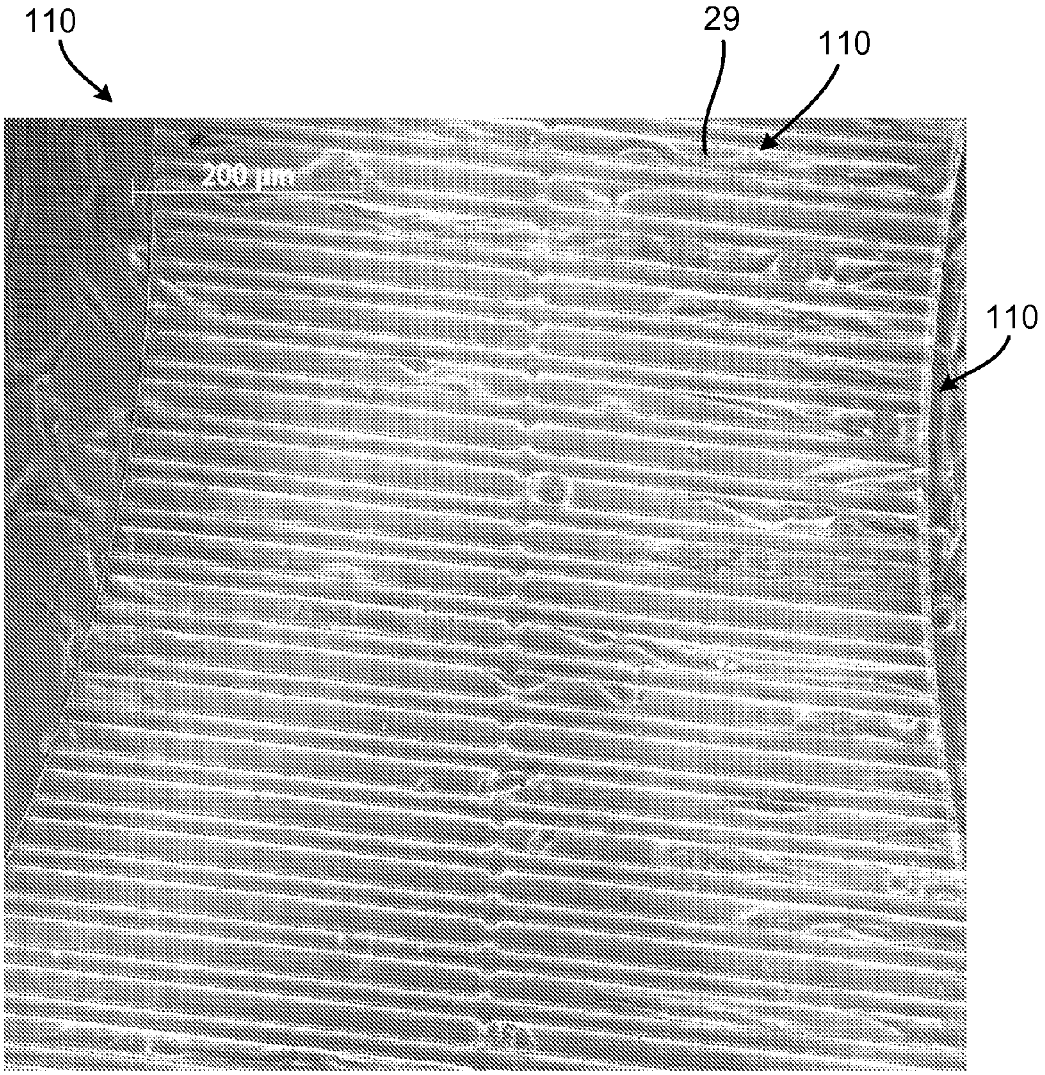
FIG. 4 is a top view of a parallel array of microcapillaries included in a fourth microfluidic device.

The migration of human cancer cells inside microcapillaries was observed. FIG. 4 is an optical micrograph showing a plurality of individual cancer cells 20 moving within a substantially parallel array of microcapillaries 130 in the absence of a chemical attractant. Time-lapse imaging can be used to record and quantify the movement of the individual cancer cells 20 through each of the microcapillaries 130. An unexpected, persistent movement of the cells at a constant speed in the absence of external gradients was noted for several hours without a reversal in their direction. The velocity and direction of movement for individual cancer cells 20 in the microcapillaries 130 was measured and recorded.

Figure 5A:
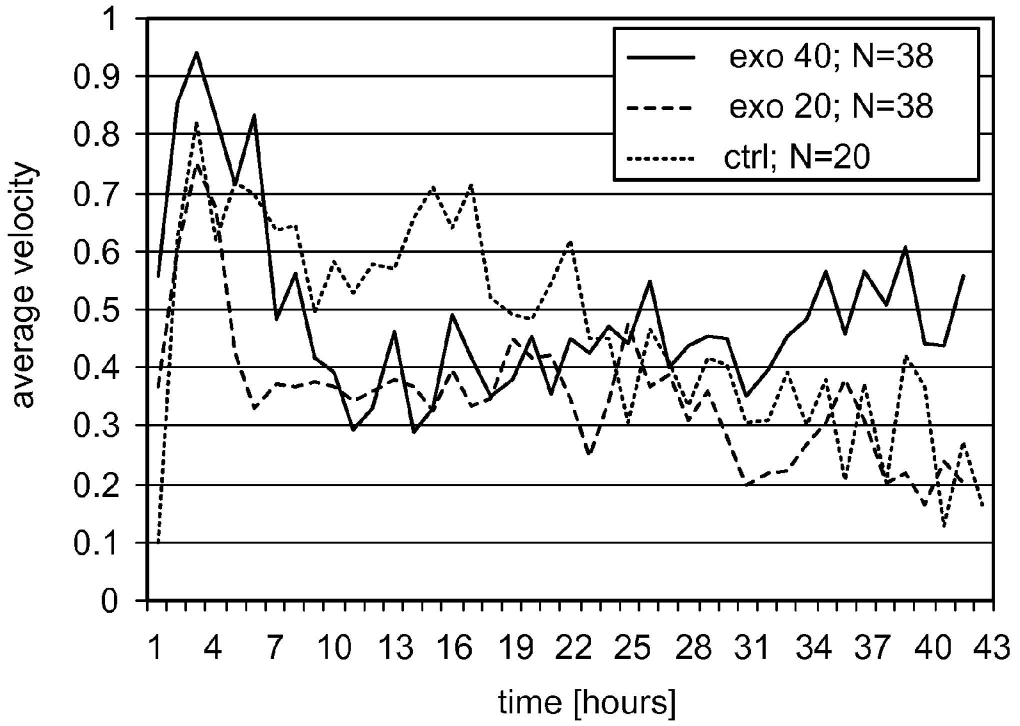
FIGS. 5A-5B are graphs showing measurements of the average velocity of cells moving through microfluidic capillaries as a function of time (FIG. 5A) and the frequency of cells in the cell population at various velocities (FIG. 5B).
Figure 5B:
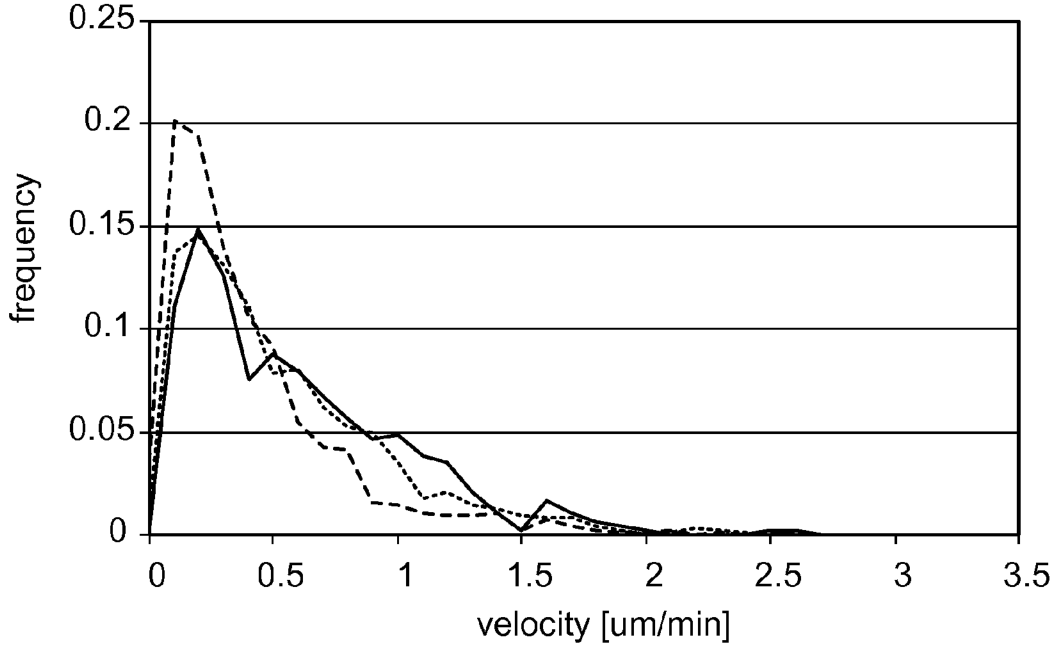

FIG. 5A is a graph showing the average velocity of cells 20 in an array of microcapillaries shown in FIG. 4. FIG. 5B is a graph showing the same population of cells 20 moving through the microcapillaries 130 as a function of cell velocity. The results in FIGS. 5A-5B are based on time-lapse imaging results to quantify the motility of the cells 20 through the microcapillaries 130 (FIG. 4) with high time and space resolution. For example, a unidirectional movement of a motile cancer cell along the length of the micropillary channel away from the opening can continue for at least six minutes.

The microfluidic motility assay can be used for methods of identifying a compound capable of mediating cell motility. These compounds can then be further screened for their potential use as anti-cancer agents. Isolated cancer cells in a reservoir 110 or microcapillary channel 130 in the devices of FIGS. 1-4 can be contacted with a chemical agent. The ability of the chemical agent to mediate cancer cell motility within the microcapillary channel 130 can be determined by observing whether the cancer cell moves within the microcapillary channel 130, or whether the movement of the cancer cell within the microcapillary channel 130 is affected by the chemical agent. For example, this approach can be used to determine if a chemical agent inhibits cancer cell motility. Accordingly, a method for identifying a compound capable of inhibiting cell motility can include contacting the isolated cancer cell test population with an opening in a microcapillary channel under conditions effective to permit a single cancer cell from the cancer cell test population to enter the microcapillary channel, the microcapillary channel opening having a cross sectional area that is smaller than the maximum cell diameter; and determining whether the chemical agent reduces the unidirectional movement of the cancer cell in the absence of a chemoattractant gradient within the microcapillary channel in a direction away from the opening, after contacting the cancer cell with the chemical agent.

Surprisingly, small number of cells were still able to migrate through the microcapillaries 130 even after exposure to microtubule destabilizing and stabilizing drugs at concentrations higher than those required to stop proliferation. We evaluated the role of microtubules in the persistent cell migration along microcapillaries. Persistent unidirectional cancer cell migration occurred in the absence of external gradients in the microcapillaries 130 described above. We tested the effect of agents that affect microtubules on cancer cell motility within microcapillaries 130. As described in Example 11, while the stabilization of microtubules with taxol in different concentration does not alter the persistent migration, microtubule destabilization with nocodazole resulted in alteration of the persistent migration behavior. The alteration is dependent on the dose of nocodazole, while even large taxol concentration. Confining the secreted molecules in the space of the microcapillary increases their concentration at one side of the cells.

In some embodiments, the microfluidic motility assay can be used as a diagnostic tool to identify highly motile cells within a heterogeneous mixture of cells. For example, cells from a tissue biopsy can be tested using the microfluidic motility assay to separate the motile cells from the non-motile cells. The motile cells can then be further screened to determine if they are normal or cancerous. Currently, biopsies are examined for morphologies indicative of cancerous cells. The microfluidic motility assay can be used to screen for cancerous cells based on motility.

Figure 6A:
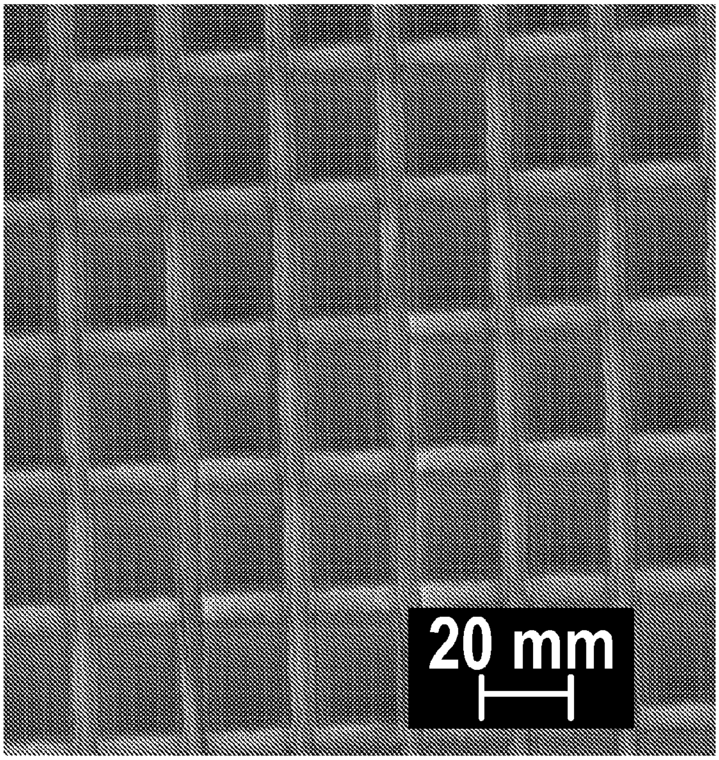
FIGS. 6A-6B are top views of microcapillaries in a fourth microfluidic device.
Figure 6B:
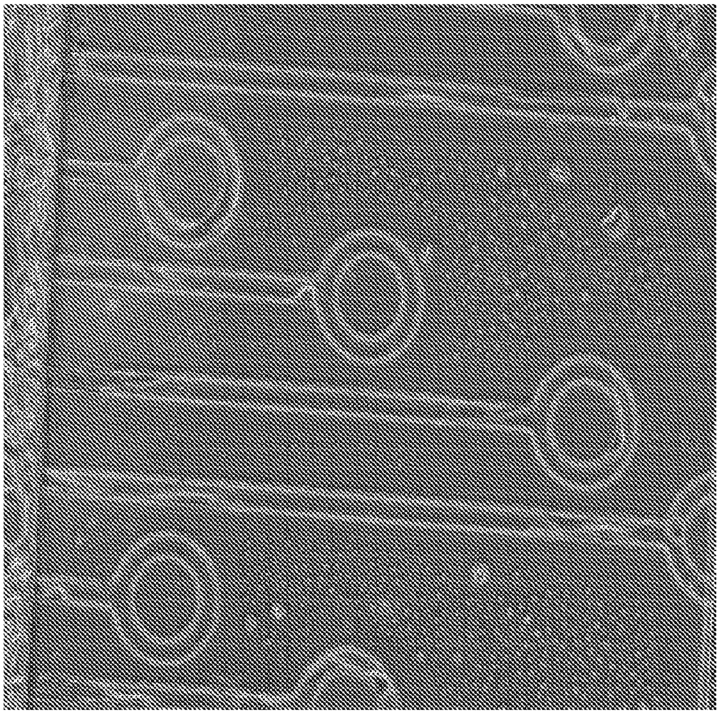

Channels of different geometries (dead end, loops, smaller transversal channels) could be implemented to model cell motility in the area of autocrine/paracrine signaling and cell-cell interaction effects of cell motility. Referring now to FIGS. 6A-6B, in alternate embodiments, microcapillaries of different sizes, shapes, and geometric connections can be employed to study aspects of cell motility. For capillaries with side channels, loops or other geometries the motility can also be quantified.

The microfluidic motility assays and methods described herein have various applications relating to cancer cell migration, and associated diagnostic and treatment methods. The persistent cell migration along predefined tracks has relevance to in vivo situations when cancer cells spread away from the primary tumor. Cancer cells often migrate along lymphatic vessels reaching the lymph nodes. In the clinical context, spreading of the cancer cells to the sentinel lymph nodes is usually a non-favorable prognostic sign prompting the need for aggressive surgical, chemical, and radiological therapy. Other cancers, like the glioblastoma migrate preferentially along white matter tracts in the brain and spreading usually happens early in the evolution of the tumor. This represents a major clinical problem and even extensive resection of the primary tumor leaves a number of cells in distant parts of the brain that will continue the cancerous process. Intraperitoneal tumors like ovarian, gastro-intestinal, or pancreatic cancer often spread throughout the peritoneal cavity, following the virtual space between peritoneal surfaces and normal routes of peritoneal fluid flow. The transcoelomic route involves the migration of cancer cells between the mesothelial cell layers, and together with the lymphatic vessels are responsible for the dissemination of the majority of gastro-intestinal and ovarian carcinomas and sarcomas. Extravascular migration of cancer cells along the periphery of blood vessels towards remote sites is also supported by histopathology evidence (Levy et al., 2009; Lugassy and Barnhill, 2007) and could have clinical implications for the treatment of melanoma and glioblastoma. Also recently, in vivo observations using cancer cells marked using fluorescent probes reported s preferential migration of cancer cells along collagen fibers (Sahai et al., 2005). Nonetheless, increasing numbers of in vitro experiments come to suggest that migration of cells under mechanical constrains is different than the migration on flat surfaces (Beningo et al., 2004), and many aspects of this behavior could be relevant to the actual migration of neutrophils through tissue in conditions of inflammation (Malawista et al., 2000) or other acquired immune responses (Lammermann et al., 2008).

The MMA provides a model of in vivo conditions and allows for better control of the conditions for cell migration. When cell migration occurs in a void microcapillary, where extracellular matrix proteins are only present on the walls, the assay is not affected by the cell abilities to degrade the matrix. Cells come into contact with the extracellular matrix throughout their entire circumference, like they would do in a regular 3D environment. At the same time, the ability of the cells to move is not restricted, at least in one direction, a more controlled situation compared to the squeezing through pores in the gel. Previous studies have suggested that in fact the porosity of the gel could be more important than the nature of the gel (Raeber et al., 2005). When capillaries are filled with matrix, the ability to directly observe cells while migrating provides information about their morphology and could help distinguish between mesenchymal and ameboid migration types. For example, recent data suggests that the difference between amoeboid and mesenchymal mode of migration could be a indication for the type of metastases that could form (Sahai and Marshall, 2003). By comparing the migration in empty and channels filled with matrix, the ability of cells to degrade the matrix could then be quantified and separated from cell motility. Potentially confounding factors include the degradation of the gel after the passage of the first cells, which leaves tracks through which other cells could follow. However, we did not measure significant differences in the speed of migration of first and subsequent cells through the same capillary, suggesting that the gel was only deformed by the first cell and not permanently degraded, and also the deformation of the gel was reversible.

Additional practical benefits from using MMA to quantify cancer cell motility are related to the restriction of migration along the predefined axis of the microcapillary. This pseudo-one dimensional migration facilitates tracking, and in combination with the parallelization of the assay in multi-well plate, could become a productive tool for screening in cell motility. The use of predefined migration tracks also allows us to observe multiple cells simultaneously, in parallel tracks, while still providing detailed single cell information. Such abilities are critically important for studying cancer cells, where metastasis are generally the result of single of few cell migration and proliferation abilities, rather than the result of average cancer cell properties. These advantages are even more important when migration assays are scaled up, and intense efforts are currently dedicated for the development of high-throughput methods for screening large libraries of cells and potential drugs.

The ability to isolate motility from the influences of other cell activities is one feature for the motility assays described herein ("MMA"), compared to existing cell migration assays. The ability to track individual cells using the MMA is not affected by cell multiplication that would confound the results from many traditional transwell or "wound healing" assays. The most common cell motility assay in use, the "Boyden chamber" or transwell (Albini and Benelli, 2007; Boyden, 1962) is an end-point assay, where the number of cells passing the membrane is a reflection not only of the cell ability to migrate but also of the rate of cell multiplication in the original or migratory populations. Similarly, the results of the "wound healing" assay (Todaro et al., 1965; Yarrow et al., 2004) are an indication not only of the ability of the cells closer to the wound to move, but they are affected by the proliferation rate of cells distant from the wound (Zahm et al., 1997). Despite its simplicity and ability to quantify cellular motility at single cell level, the wound healing assay is performed on flat surfaces and its relevance to the behavior of cancer cells in tissues is limited (Decaestecker et al., 2007; Wang et al., 1998). Most often, in vivo assays using sophisticated imaging systems are performed to track individual cells moving away from the primary tumor site (Condeelis and Segall, 2003). However efforts towards precise quantification are hampered by the natural variability and complexity of the microenvironment conditions experienced by the moving cells (Friedl and Wolf, 2003) and by the close or distant interaction with other cells (Condeelis and Segall, 2003). These conditions are better controlled in in vitro assays which rely on the use of gels to create 3D-like environments (Lee et al., 2008; Yamada and Cukierman, 2007). However, only a small number of cells can be tracked at once, e.g. gel invasion assay (Demou and McIntire, 2002), and cell migration is highly dependent on the ability of the cells to degrade the particular matrix used in the assay (Even-Ram and Yamada, 2005).

EXAMPLES

Example 1

Constructing a Microcapillary Motility Assay Device

Figure 7A:
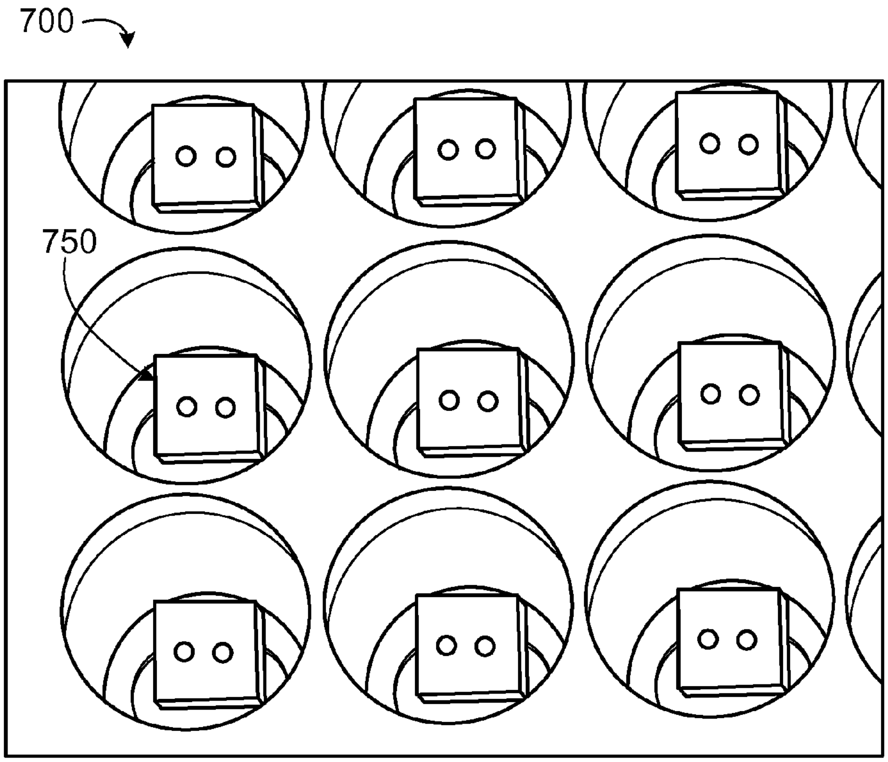
FIGS. 7A-7B shows a fifth microfluidic device with an array of microfluidic channels.
Figure 7B:
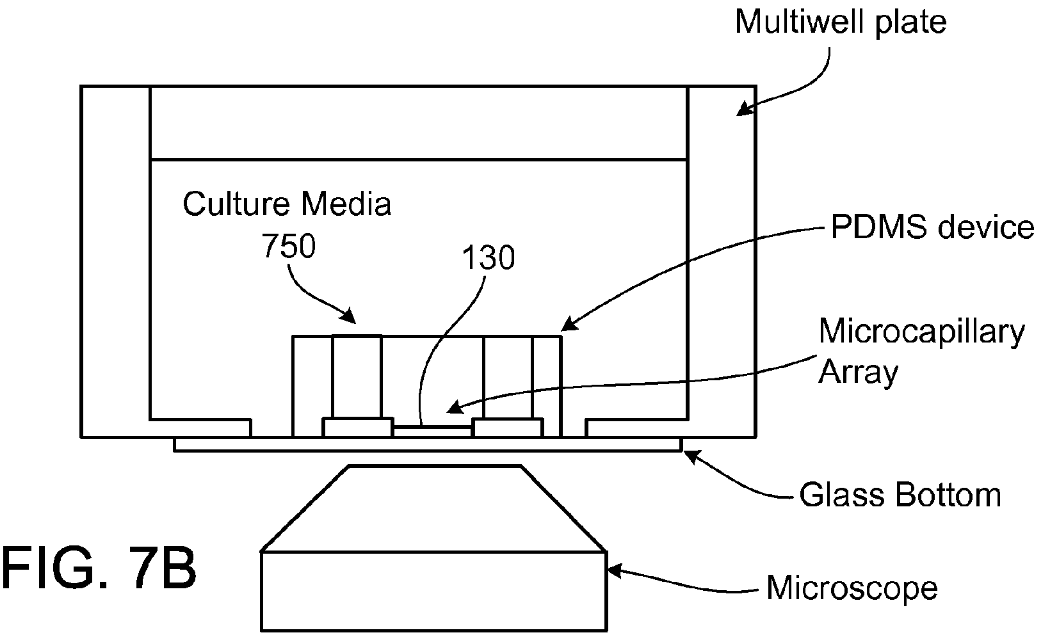

Referring now to FIGS. 7A-7B, a microcapillary motility assay (MMA) device 700 including microfluidic devices 750 were manufactured by casting polydimethyl siloxane (PDMS, Dow Corning, Midland. Mich.) on a microstructured mold. The microstructured mold was fabricated using standard photolithographic technologies. A silicon wafer was coated with a 10 μm thin layer of photoresist (SU8, Microchem, Newton, Mass.) and processed following the standard protocol as recommended by the manufacturer. A second, thicker layer of approximately 50 μm was then photopatterned on the same wafer and aligned with respect to the first layer in order to define the connections between the capillaries and the wells. The mold was placed in a Petri-dish and covered with PDMS freshly prepared according to the manufacturer's instructions. After baking for 8 hours at 65° C., the cast PDMS was removed from the mold, one microwell for each device was punched using a 2 mm puncher, and each device was cut using a 5 mm puncher. After exposure for 20 seconds to oxygen plasma in a plasma asher (March, Concord, Calif.), the devices were individually bonded on the coverslips at the bottom of 24-well plates (Mattek, Ashland, Mass.).

After bonding, and while the PDMS was still hydrophilic, 2 μL of a solution of 2 μg/mL collagen IV was added inside the center microwell of each device. The strong capillary force ensured the collagen solution filled the capillaries. Excess collagen was later washed away by adding 5 μL of phosphate buffer (PBS) in only one well of the devices. Alternatively, 2 μL of Matrigel (BD Biosciences, San Jose, Calif.) was added in one well at 4° C. and the entire plate was heated to 37° C. for 5 minutes.

Example 2

Microcapillary Motility Assay (MMA)

The movement of various individual cancer cells from different cell lines listed in Table 1 were observed in the microcapillaries of the device of Example 1 by performing microcapillary motility assays (MMA) as described below. Seven cancer cell lines were purchased from ATCC and cultured according to the recommended protocols.

TABLE 1

| Cancer cell lines | | |
|---|---|---|
| Designation | Source | Culture media |
| H1650 | Lung adenocarcinoma | RPMI1640 with 10% FBS and 1% PenStrep |
| H446 | Lung carcinoma | RPMI1640 with 5% FBS and 1% PenStrep |
| PCS | Prostate adenocarcinoma | F-12K with 10% FBS and 1% PenStrep |
| LnCaP | Prostate carcinoma | RPMI1640 with 10% FBS and 1% PenStrep |
| MDA-MB 231 | Breast adenocarcinoma | DMEM with 10% FBS and 1% PenStrep |
| U-87 MG | Glioblastoma | EMEM with 10% FBS and 1% PenStrep |
| HT-29 | Colorectal adenocarcinoma | McCoy's 5a with 10% FBS and 1% PenStrep |

Before performing each migration assay, cells growing in cell culture flasks were washed with PBS, lifted from the surface using trypsin or 10 mM calcium chelator solution in buffer (EDTA, Sigma Aldrich, St. Louis, Mo.), suspended into 10 mL of media, centrifuged, and re-suspended into media at $10^6$ cells/mL. Cells were then seeded in one well of each device, by directly pipetting 3-4 μL of the cell suspension in each well. After loading the cells, 3 mL of corresponding media were added to each well of the multi-well plate, completely covering the devices.

MMA is compatible with the use of chemical gradients driving cell motility, although chemical gradients are not required to observe migration of motile cancer cells in the MMA. One approach is to load gel beads loaded with the target compound in one well and cells into the second well. A gradient will form through the capillaries connecting the two wells in no-flow conditions.

To image the moving cells, the multi-well plate was placed on the motorized stage of a Zeiss Axiovert microscope fitted with an environmental chamber. The environment was set at 37.7° C. and 5% CO2. Cells were imaged using 10× objective and phase contrast. Three separate images from each array were acquired every 6 minutes for 24-48 hours. Because cell motility is restricted only along the capillary, in one linear dimension, the motility is easy to image and easy to quantify for extended periods of times. We have tracked cells for more than 72 hours.

Direct observation of cells in the MMA allows recording the size, morphology of cells during migration (ameboid vs mesenchymal), single vs clusters of cells. Intracellular clues (e.g. protein localization in the cytoplasm vs nucleus, cytoskeleton markers, etc) could be followed in heterogeneous populations through the use of fluorescent markers.

To quantify the migration of individual cells, images were analyzed using the manual tracking function in the Image J software. The middle of cells was tracked through the series of frames and only cells entering the microcapillaries were tracked. At least 50 cells migrating through the capillaries were tracked for each condition. Average velocity over 12 hours was calculated from temporary velocities over each 6 minutes interval and presented as mean and standard error of the mean.

Further analysis of data was performed in Excel and Sigma Plot. Results for populations are presented as median, box for 25 to 75 percentile, whiskers at 5 and 95 percentile and outliers as dots. The boundary of the box closest to zero indicates the 25th percentile, a line within the box marks the median, and the boundary of the box farthest from zero indicates the 75th percentile. Error bars above and below the box indicate the 90th and 10th percentiles. Individual dots represent outliers. Comparisons between populations were performed using T-test and 5% confidence interval.

The microfluidic microcapillary motility assay (MMA) enabled us to simultaneously run several independent migration assays in 12 or 24 well array format (FIGS. 7A-7B). We measured the migration of hundreds of cancer cells at single cell level over periods of time from 3 to 72 hours, at 6 minutes time resolution. Our experience shows that good statistical data could be obtained from as few as 50 cells.

Example 3

MMA Using MDA-MB 231 Breast Cancer Cells

We developed microcapillary motility assay (MMA) for cancer cell motility using the device described in Example 1 that allowed us to directly observe and quantify cancer cell migration at single cell level with very high spatial and temporal resolution. We made the unexpected observation that when cancer cells from different human cell lines are mechanically constrained inside microcapillaries of size comparable with cell sizes, they can move persistently in one direction for several hours. We observed a large dispersion of the motility abilities of cells from different cancer cell lines and within the same cell line, with some cells moving faster than 150 μm/hour. This migration speed is the equivalent of approximately 10 cm in one month, consistent with the ability of many cancer cells to invade distant sites.

Figure 8A:
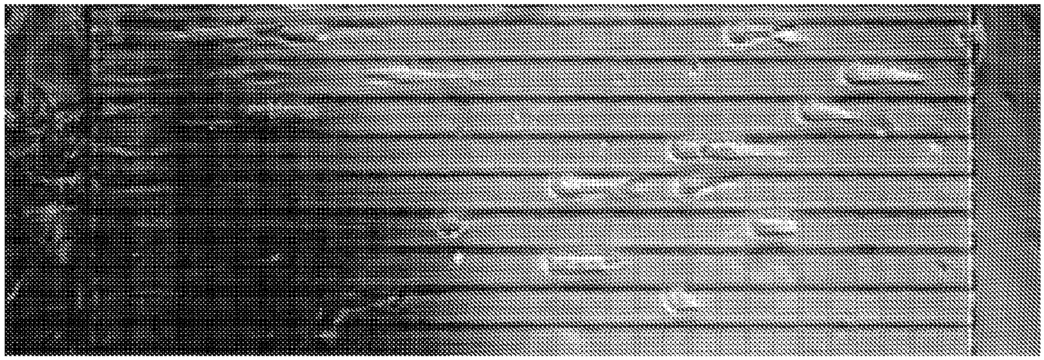
FIG. 8A is an optical micrograph of MDA-MB231 breast cancer cells moving within microcapillaries in a sixth microfluidic device.
Figure 8B:
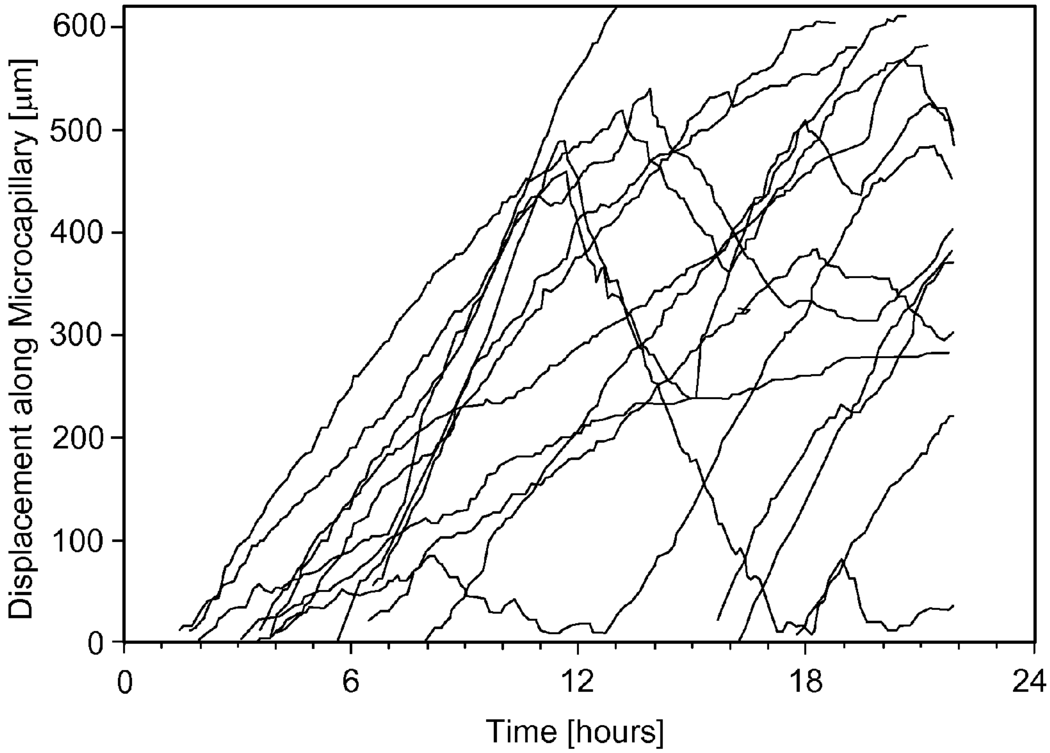
FIG. 8B is a graph showing the displacement vs. time of multiple MDA-MB231 breast cancer cells inside the microcapillaries of the sixth microfluidic device.

Using the assay described in Example 2, and the device described in Example 1, we tracked individual MDA-MB 231 breast cancer cells while migrating inside collagen-coated microcapillaries. FIG. 8A shows MDA-MB231 breast cancer cells in microcapillaries; FIG. 8B is a graph showing the displacement of these breast cancer cells plotted against time. Cells in FIG. 8A moved persistently away from the cell seeding reservoir and reversals of direction are comparatively rare (as seen from the data shown in the graph in FIG. 8B). The shape of the fast moving cells was mostly "ameboid," while slower moving cells were mostly of the "mesenchymal" shape. Single cell tracking revealed unexpected persistence for several hours in one direction. Many cells moved from end to the other of the capillaries without stopping or changing direction. We also observed some cells turning back when reaching the distal end of the capillary and then migrating towards the center well. Interestingly, the migration of cancer cells coming back towards the center well was quantitatively measured to have the same velocity as the initial centrifugal migration. Cells moved at an. We only considered cells migrating freely, without interactions with other cells. Also, cells that divided during the experiment were excluded from the analysis.

Figure 9A:
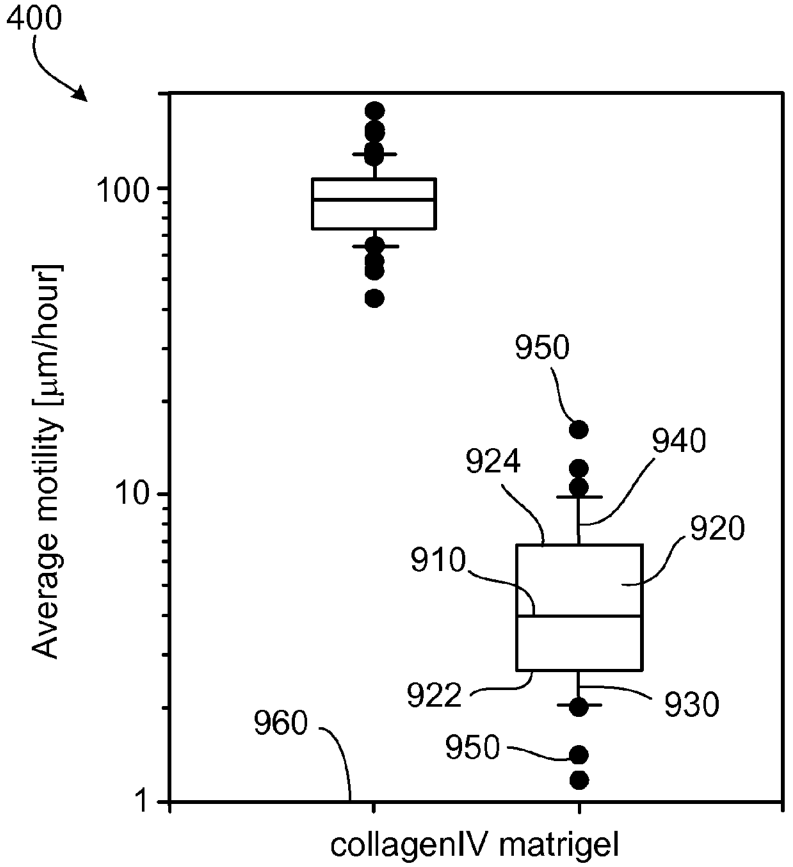
FIG. 9A is a graph showing the differences in the average motility of MDA-MB231 breast cancer cells migrating in collagen IV coated microcapillaries and Matrigel filled microcapillaries.
Figure 9B:
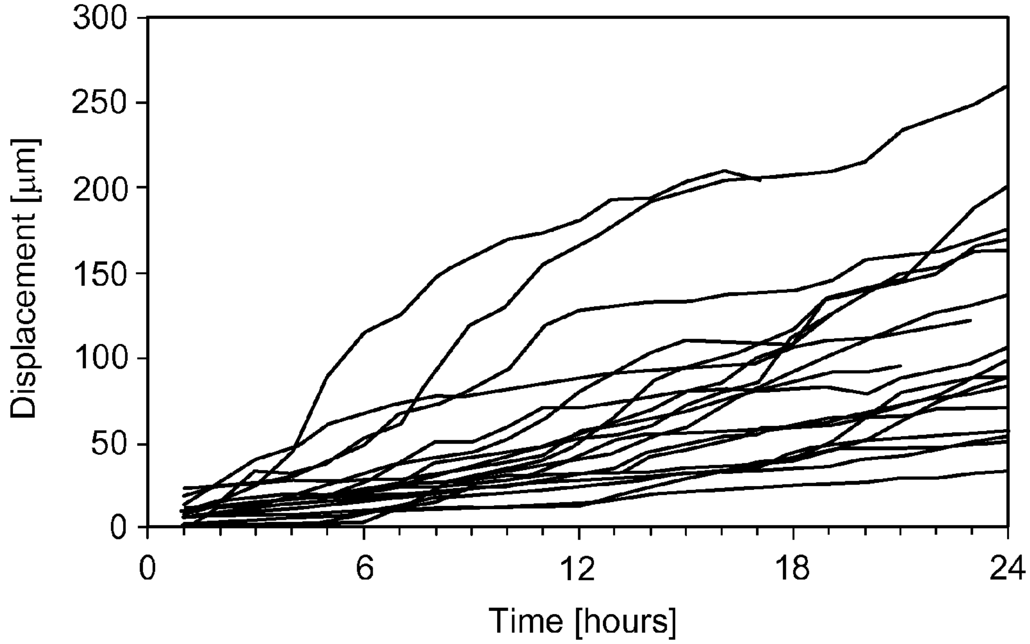
FIG. 9B depicts a graph showing the displacement vs. time of multiple MDA-MB231 breast cancer cells inside the Matrigel filled microcapillaries of a microfluidic device.

To better understand the effect of mechanical constrains on cancer cells we tested the migration of MDA-MB231 breast cancer cells in capillaries filled with MATRIGEL. FIG. 9A is a graph showing the difference in the average motility of MDA-MB231 breast cancer cells measured for migration through empty capillaries compared to migration in capillaries filled with MATRIGEL. As shown in the graph in FIG. 9B of cellular displacement of MDA-MB231 breast cancer cells along the microchannel as a function of time, the velocity of cell migration decreased by an order of magnitude in MATRIGEL, but the persistence of migration was maintained.

MDA-MB231 breast cancer cells in microcapillaries coated with collagen IV migrated at 94.0±3.6 μm/hour moved significantly faster than cells moving inside Matrigel filled capillaries (5.1±0.7 μm/hour). We observed cell migration using phase contrast microscopy and noted that the cells moving through the Matrigel filled microcapillaries do not completely fill the capillaries and instead squeeze through smaller spaces. This behavior suggests that MDA-MB231 breast cancer cells move through Matrigel by a combination of squeezing and matrix degradation.

Figure 12:
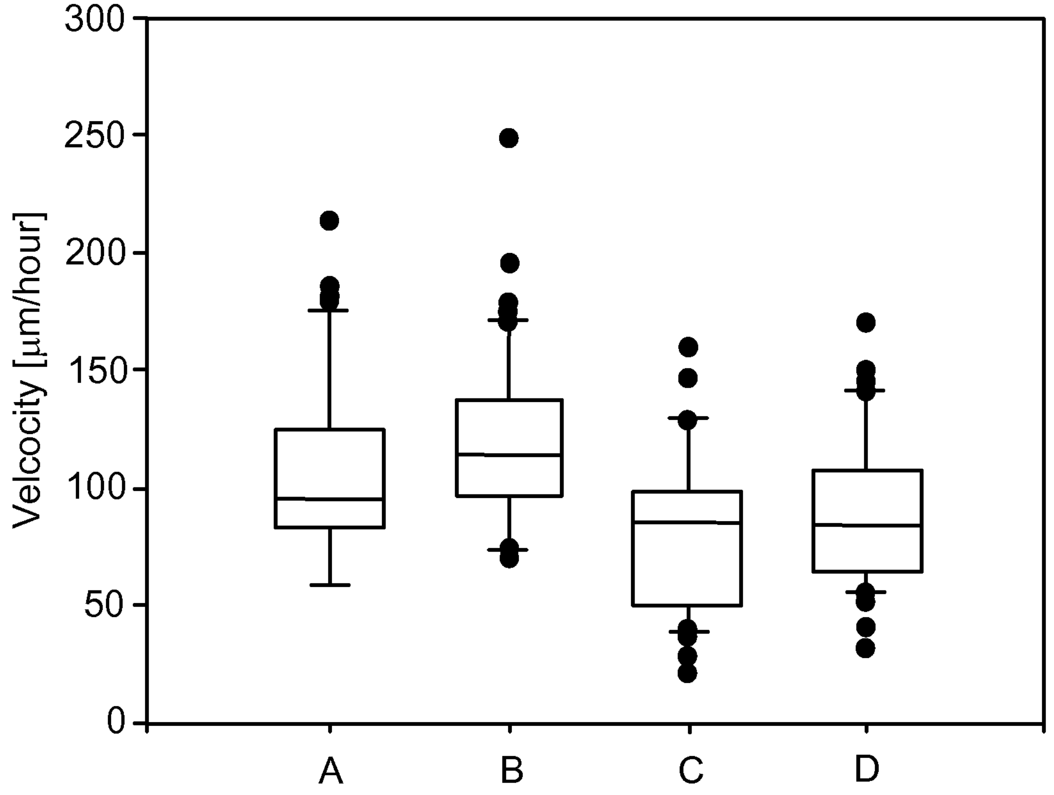
FIG. 12 is a graph comparing cell motility of MDA-MB231 breast cancer cell in different conditions.

FIG. 12 is a graph comparing cell motility of MDA-MB231 breast cancer cell in different conditions. We found no significant difference in motility inside smaller (6×10 μm) compared to larger (20×10 μm) channels. We also found no significant difference in motility through channels coated with collagen IV and fibronectin. The only significant difference was due to differences in the protocol lifting the cells from the cell culture dish. Cells that were released using a calcium chelator moved on average faster than the cells released using trypsin.

Examples 4-10

MMA Using Various Cancer Cell Lines

Figure 10:
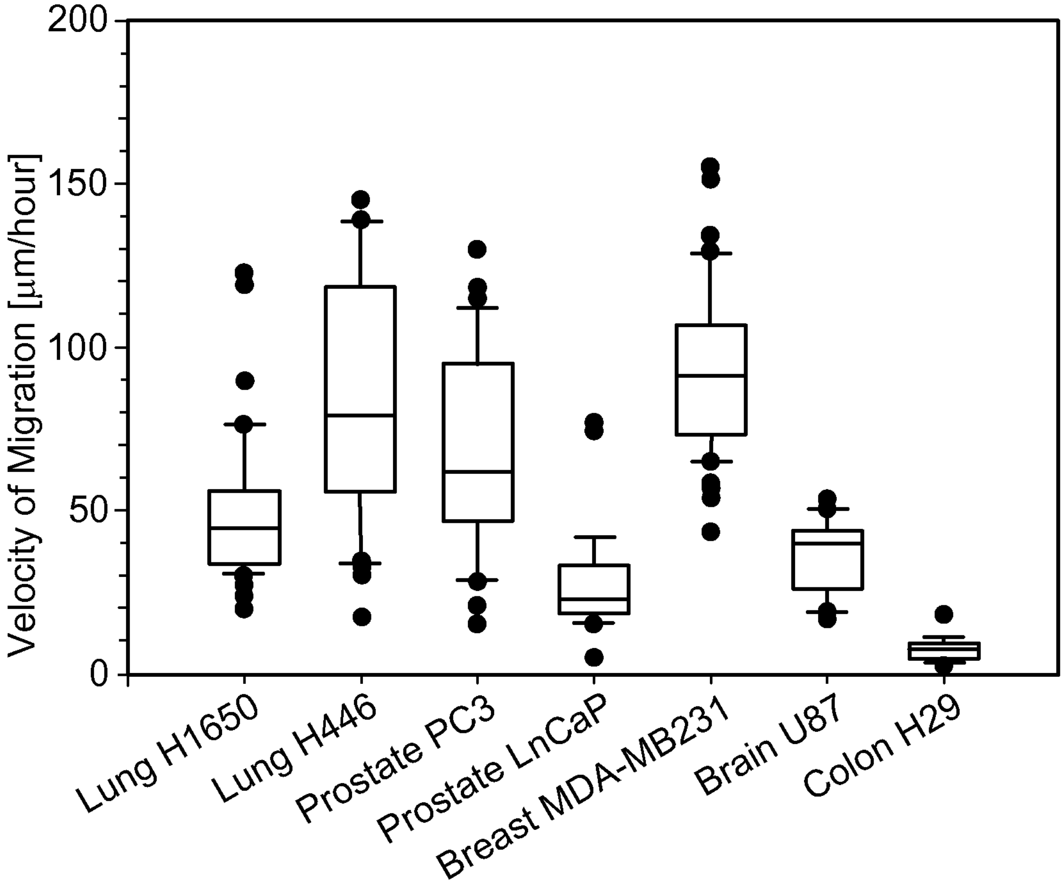
FIG. 10 depicts a graph showing a comparison in the average motility of seven types of cancer cells migrating in collagen IV coated microcapillaries, in accordance with exemplary embodiments.

We also used MMA described in Example 2 and the device described in Example 1 to measure motility in several human cancer cell lines: lung cancer H1650 (Example 4), lung cancer H446 (Example 5), Prostate cancer PC3 (Example 6), Prostate cancer LnCaP (Example 7), Breast cancer MDA-MB231 (Example 8), brain cancer U87 (Example 9), and colon cancer H29 (Example 9). Results are summarized in the graph in FIG. 10. Minimal changes in the size of the channels are required to accommodate cells of different types. We have observed no significant difference in motility of MDA-MB231 breast cancer cell line in 6×10 vs 20×10 μm microcapillaries.

The motility of cells originating from prostate, breast, lung, colon and brain was measured for at least 12 hours in at least 3 microcapillary arrays. Motility was the highest for the NCI-H446 lung cancer (average speed 85.7±6.7 μm/hour, N=40), PC3 prostate cancer (average speed 67.8±4.9 μm/hour, N=40) and MDA-MB231 breast cancer lines (average speed 94.0±3.6 μm/hour, N=56) and lower in other cell lines: lung carcinoma H1650 (average speed 49.5±3.6 μm/hour, N=40), prostate carcinoma LnCaP (average speed 28.0±3.4 μm/hour, N=24), glioblastoma U87 (average speed 36.4±2.5 μm/hour, N=20), or colon adenocarcinoma H29 (average speed 7.5±1.1 μm/hour, N=13). Interestingly, a small number of cells displayed average velocities that were in excess of 100 μm/hour for the entire length of the microcapillaries. This surprisingly fast motility of cancer cells was recorded in empty microcapillaries coated with collagen IV, and in the absence of limitations from a dense matrix or cell-cell interactions.

Example 11

MMA Using Agents to Alter Microtubule Dynamics

To probe into the mechanisms responsible for persistent cell migration, we exposed the cells to drugs that alter microtubule dynamics while performing the MMA described in Example 2 using the microfluidic device shown in FIG. 2.

Figure 11:
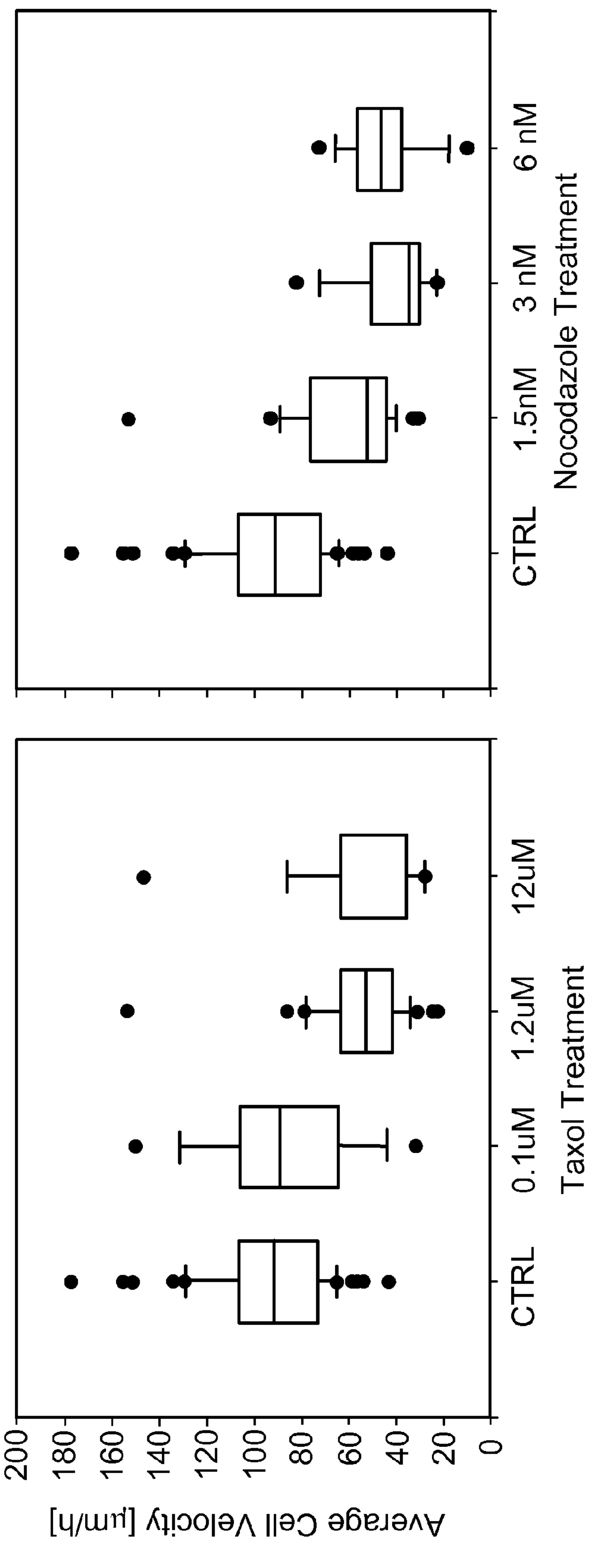
FIG. 11 depicts a graph showing a comparison in the average motility of MDA-MB231 breast cancer cells migrating in collagen IV coated microcapillaries, when exposed to differing concentrations of Taxol and Nocodazole, in accordance with exemplary embodiments.

FIG. 11 shows the effects of paclitaxel ("Taxol Treatment") and nocodazole ("Nocodazole Treatment") on MDA-MB231 breast cancer line. Paclitaxel (i.e., Taxol) inhibited persistent motility at concentrations above 100 ng/mL and Nocodazole at concentrations above 0.5 ng/mL. Only Nocodazole at concentrations above 1 ng/mL inhibited the migration of the fastest moving cells.

The device has been used with several cell types. Channels can have different size, and can be coated with different extracellular matrix proteins. The effect of different drugs on cell motility can be explored.

TABLE 2

Effect of Microtubule-Altering Agents on Cell Motility in MMA

| Cell Line Type | Origin | Drugs tested | Channel size |
|---|---|---|---|
| U87 | glioblastoma | | 20 μm wide × 8 μm tall |
| MD231 | breast cancer | Nocodazole, Taxol | 6 μm wide × 10 μm tall |
| MCF10 | breast cancer | | 6 μm wide × 10 μm tall |
| HCC | breast cancer | | 6 μm wide × 10 μm tall |
| H1650 | Lung cancer | Taxol | 10 μm wide × 8 μm tall |
| H446 | Lung cancer | | 10 μm wide × 8 μm tall |
| 621 | Lung cancer | | 10 μm wide × 8 μm tall |
| HT29 | Colon cancer | | 10 μm wide × 8 μm tall |
| PCS | prostate cancer | Taxol | 10 μm wide × 8 μm tall |
| LNCaP | prostate cancer | Taxol | 10 μm wide × 8 μm tall |
| VCap | prostate cancer | Taxol | 10 μm wide × 8 μm tall |
| SYS | neuroblastoma | | 10 μm wide × 8 μm tall |
| PC12 | neuroblastoma | | 10 μm wide × 8 μm tall |

We observed that both taxol and nocodazole significantly decrease the speed of cancer cell migration through the microcapillary array. The dose response shows a significant decrease in motility between 100 nM and 1 μM for Taxol, and bellow 100 nM for Nocodazole. However, one could notice that even at the higher concentrations of Taxol, between 1 and 10 μM, some cells managed to move faster than 100 μm/hour. Although only the number of fast moving cells is low these cells may be successful in traversing large distances in tissues and establishing metastasis. The effect of these cells on the average velocity is small, but their clinical and biological importance may be higher than the average cells. Nocodazole in concentrations larger than 1° μM significantly altered the speed of migration for all cells in the population.

Figure 13:
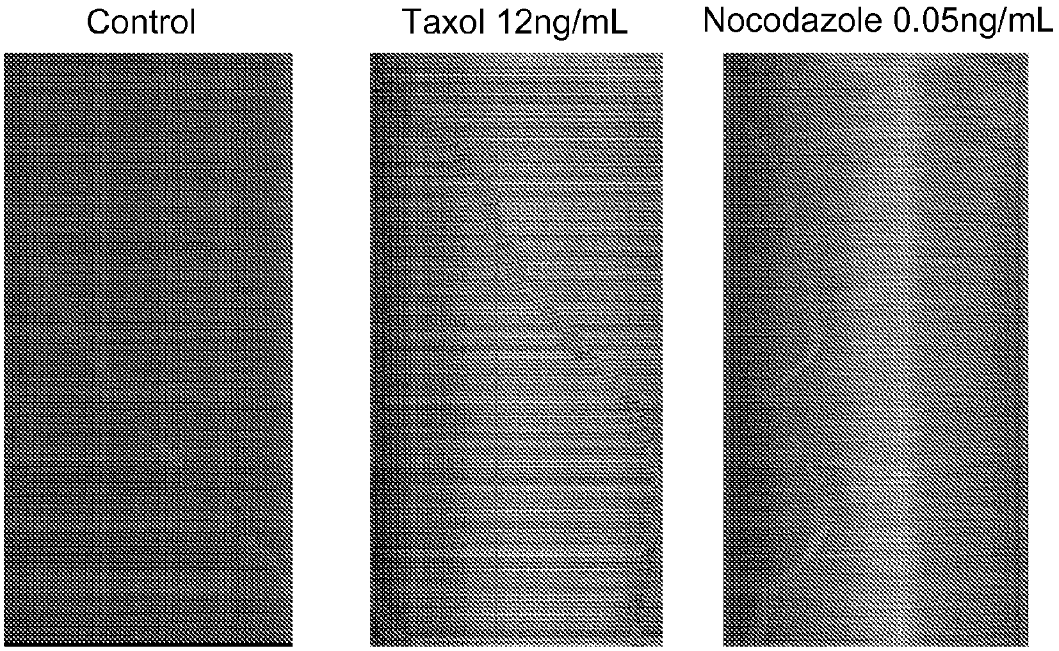
FIG. 13 shows a Kymograph analysis of single cell motility assay over 18 hour period.

FIG. 13 shows a Kymograph analysis of single cell motility over 18 hour period. Typical control and taxol treated cells (12 nM) show persistent movement along the microcapillary. Only the control cell leaves the microcapillary while the taxol treated cells reverses direction at the end of the microcapillary. The nocodazole treated cell (0.05 ng/mL) displays frequent changes of direction and less persistence, as well as alterations in cell length during the migration.

Example 12

Assessing MDA-MB-231 Invasion and Migration In Vitro with Stable MYC Knockdown

We also used embodiments of the microfluidic device to probe whether MYC activity was necessary for cancer cell invasion or migration. Each device contained an array of linear micro-capillaries that were each 10 μm tall, 20 μm wide, and 600 μm long. The microcapillary arrays were manufactured as described above. Immediately after bonding, and while the PDMS was still hydrophilic, devices were immediately coated with either Matrigel or collagen IV.

Individual MDA-MB-231 cells were visualized using live-cell, time-lapse, video-microscopy, after seeding into micro-capillaries either filled with Matrigel (to simulate some of the 3-dimensional microenvironmental conditions that cancer cells encounter in vivo) or simply coated with collagen IV (to study unimpeded migration). Within a few hours after device fabrication, 2 μl of cell suspension was loaded in the device at 106-107 cells/ml, and individual wells on the plate filled with 3 ml of media (DMEM, 10% FCS) completely covering the microfluidic devices. The multiwell plate was mounted on the automated stage of an Axiovert Zeiss microscope, equipped with an environmental chamber set at 37° C. and 5% CO2. Cells were imaged using a 10× objective and phase contrast with individual frames acquired from 3 different locations of each device every 6 minutes for 24-72 hours.

Figure 14A:
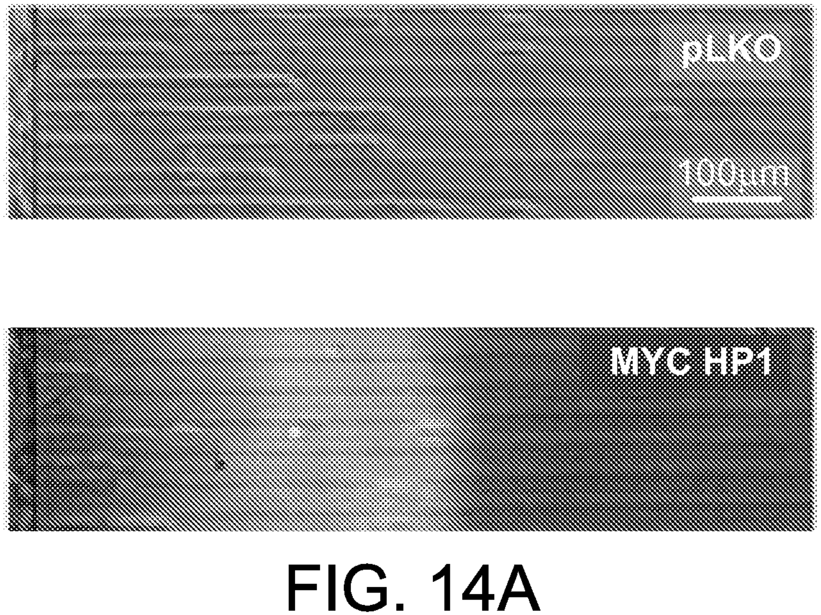
FIGS. 14A-F show results of an assessment of MDA-MB-231 invasion and migration in vitro with stable MYC knockdown.

These experiments were specifically performed in the absence of a chemo-gradient, thus allowing us to examine intrinsic cell behavior. Quantitative analysis of single-cell velocities in this device revealed that MYC knockdown greatly impeded MDA-MB-231 invasion in Matrigel but only had mild effects on migratory velocities compared to control cells. FIG. 14A presents representative light microscopic images of control (pLKO) and MYC knockdown (MYC HP1) MDA-MB-231 breast cancer cells migrating through Matrigel-filled micro-capillaries. FIG. 14B presents the position of individual pLKO and MYC HP1 cells invading through Matrigel-filled micro-capillaries over 24 hours plotted against time. FIG. 14C presents the average invasion distance through Matrigel for pLKO and MYC HP1 cells; 13.9±1.1 μm/hour for pLKO (N=33, ±SEM) and 9.1±0.9 μm/hour for MYC HP1 (N=31, ±SEM) and 10.9±0.7 μm/hour for MYC HP2 (N=33, ±SEM). P-values are computed by two-sided Walsh t-test.

Figure 14D:
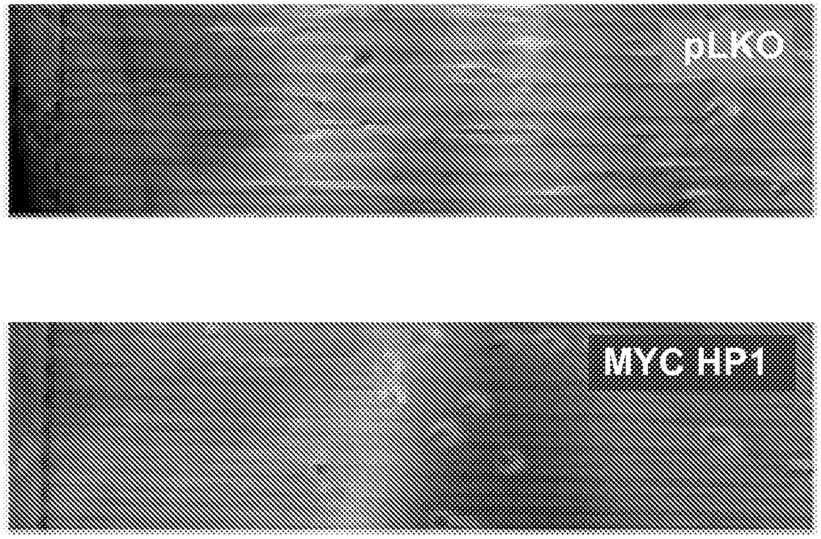
Figure 14B:
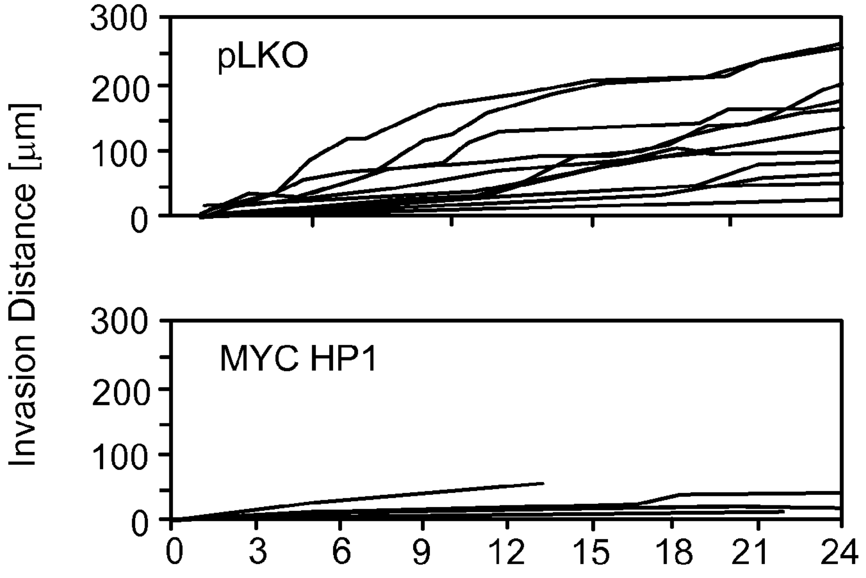
Figure 14C:
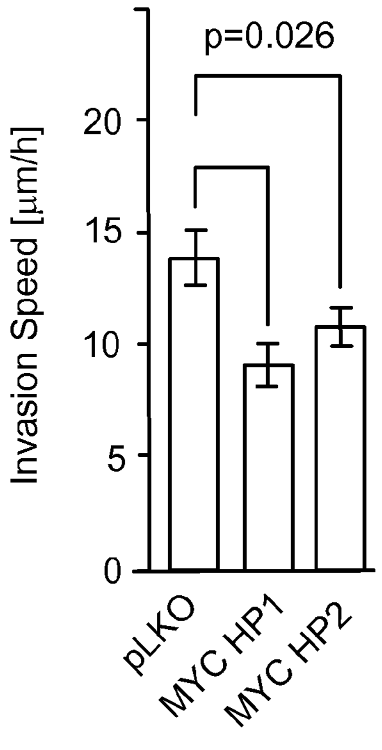
Figure 14E:
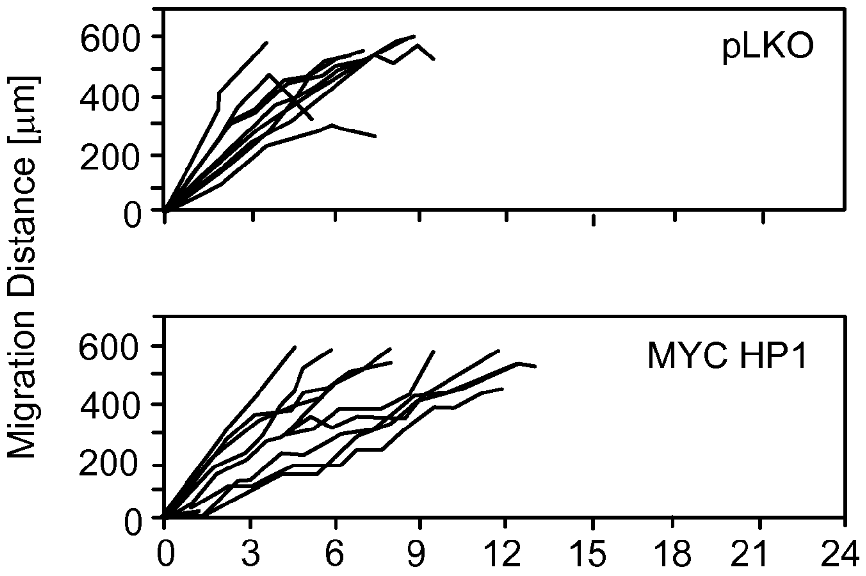
Figure 14F:
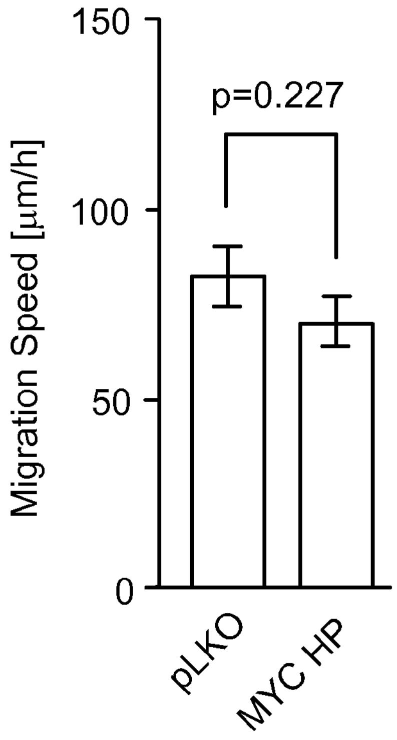

FIG. 14D presents representative light microscopic images of pLKO and MYC HP1 MDA-MB-231 breast cancer cells migrating through collagen IV coated microcapillaries. FIG. 14E presents the position of individual pLKO and MYC HP1 cells migrating along collagen IV coated micro-capillaries over 12 hours plotted against time. FIG. 14F presents the average migration distance through collagen coated micro-capillaries for pLKO and MYC knockdown cells; 82.5±7.5 μm/hour for pLKO (N=17, ±SEM) and 70.4±6.4 μm/hour for MYC HP1 (N=21, ±SEM). P-value is computed by two-sided Walsh t-test.

As was most evident in the time-lapse movies of migrating cells, however, knockdown cells were rounded, moved less efficiently and persistently, made frequent and disordered changes in direction compared with control cells, and did not exit micro-capillaries efficiently. The quantitative effect of MYC knockdown on MDA-MB-231 cell invasion was also assessed in more traditional Boyden chamber assays. We found that MYC knockdown in this experimental system lead to an approximately 50% decrease in invasion. These findings demonstrated that in highly metastatic MDA-MB-231 breast cancer cells, MYC is necessary to specifically maintain an invasive and migratory state.

REFERENCES

Albini, A., and R. Benelli. 2007. The chemoinvasion assay: a method to assess tumor and endothelial cell invasion and its modulation. *Nat Protoc* 2 (3):504-511.

Beningo, K. A., M. Dembo, and Y. L. Wang. 2004. Responses of fibroblasts to anchorage of dorsal extracellular matrix receptors. *Proc Natl Acad Sci USA* 101 (52):18024-18029.

Boyden, S. 1962. Chemotactic Effect of Mixtures of Antibody and Antigen on Polymorphonuclear Leucocytes. *Journal of Experimental Medicine* 115 (3):453-&.

Carmignani, C. P., T. A. Sugarbaker, C. M. Bromley, and P. H. Sugarbaker. 2003. Intraperitoneal cancer dissemination: mechanisms of the patterns of spread. *Cancer Metastasis Rev* 22 (4):465-472.

Cavallaro, U., and G. Christofori. 2004. Cell adhesion and signalling by cadherins and Ig-CAMs in cancer. *Nat Rev Cancer* 4 (2):118-132.

Chiang, A. C., and J. Massague. 2008. Molecular basis of metastasis. *N Engl J Med* 359 (26):2814-2823.

Condeelis, J., and J. E. Segall. 2003. Intravital imaging of cell movement in tumours. *Nature Reviews Cancer* 3 (12):921-930.

Decaestecker, C., O. Debeir, P. Van Ham, and R. Kiss. 2007. Can anti-migratory drugs be screened in vitro? A review of 2D and 3D assays for the quantitative analysis of cell migration. *Medicinal Research Reviews* 27 (2):149-176.

Demou, Z. N., and L. V. McIntire. 2002. Fully automated three-dimensional tracking of cancer cells in collagen gels: Determination of motility phenotypes at the cellular level. *Cancer Research* 62 (18):5301-5307.

Even-Ram, S., and K. M. Yamada. 2005. Cell migration in 3D matrix. *Current Opinion in Cell Biology* 17 (5):524-532.

Feki, A., P. Berardi, G. Bellingan, A. Major, K. H. Krause, P. Petignat, R. Zehra, S. Pervaiz, and I. Irminger-Finger. 2009. Dissemination of intraperitoneal ovarian cancer: Discussion of mechanisms and demonstration of lymphatic spreading in ovarian cancer model. *Crit Rev Oncol Hematol.*

Friedl, P., and K. Wolf. 2003. Tumour-cell invasion and migration: Diversity and escape mechanisms. *Nature Reviews Cancer* 3 (5):362-374.

Gerhardt, H., and H. Semb. 2008. Pericytes: gatekeepers in tumour cell metastasis? *Journal of Molecular Medicine—Jmm* 86 (2):135-144.

Giese, A., and M. Westphal. 1996. Glioma invasion in the central nervous system. *Neurosurgery* 39 (2):235-250.

Hanahan, D., and R. A. Weinberg. 2000. The hallmarks of cancer. *Cell* 100 (1):57-70.

Irimia, D., G. Balazsi, N. Agrawal, and M. Toner. 2009. Adaptive-Control Model for Neutrophil Polarization in the Direction of Chemical Gradients. *Biophysical Journal* in press.

Irimia, D., G. Charras, N. Agrawal, T. Mitchison, and M. Toner. 2007. Polar stimulation and constrained cell migration in microfluidic channels. *Lab Chip* 7 (12):1783-1790.

Lammermann, T., B. L. Bader, S. J. Monkley, T. Worbs, R. Wedlich-Soldner, K. Hirsch, M. Keller, R. Forster, D. R. Critchley, R. Fassler, and M. Sixt. 2008. Rapid leukocyte migration by integrin-independent flowing and squeezing. *Nature* 453 (7191):51-55.

Lee, S. H., J. J. Moon, and J. L. West. 2008. Three-dimensional micropatterning of bioactive hydrogels via two-photon laser scanning photolithography for guided 3D cell migration. *Biomaterials* 29 (20):2962-2968.

Levy, M. J., F. C. Gleeson, and L. Zhang. 2009. Endoscopic ultrasound fine-needle aspiration detection of extravascular migratory metastasis from a remotely located pancreatic cancer. *Clin Gastroenterol Hepatol* 7 (2):246-248.

Lugassy, C., and R. L. Barnhill. 2007. Angiotropic melanoma and extravascular migratory metastasis: a review. *Adv Anat Pathol* 14 (3):195-201.

Malawista, S. E., A. de Boisfleury Chevance, and L. A. Boxer. 2000. Random locomotion and chemotaxis of human blood polymorphonuclear leukocytes from a patient with leukocyte adhesion deficiency-1: normal displacement in close quarters via chimneying. *Cell Motil Cytoskeleton* 46 (3):183-189.

Overall, C. M., and C. Lopez-Otin. 2002. Strategies for MMP inhibition in cancer: innovations for the post-trial era. *Nat Rev Cancer* 2 (9):657-672.

Raeber, G. P., M. P. Lutolf, and J. A. Hubbell. 2005. Molecularly engineered PEG hydrogels: a novel model system for proteolytically mediated cell migration. *Biophys J* 89 (2): 1374-1388.

Rhee, S., H. Jiang, C. H. Ho, and F. Grinnell. 2007. Microtubule function in fibroblast spreading is modulated according to the tension state of cell-matrix interactions. *Proc Natl Acad Sci USA* 104 (13):5425-5430.

Sahai, E. 2007. Illuminating the metastatic process. *Nature Reviews Cancer* 7 (10):737-749.

Sahai, E., and C. J. Marshall. 2003. Differing modes of tumour cell invasion have distinct requirements for Rho/ROCK signalling and extracellular proteolysis. *Nat Cell Biol* 5 (8):711-719.

Sahai, E., J. Wyckoff, U. Philippar, J. E. Segall, F. Gertler, and J. Condeelis. 2005. Simultaneous imaging of GFP, CFP and collagen in tumors in vivo using multiphoton microscopy. *Bmc Biotechnology* 5.

Savage, P., J. Stebbing, M. Bower, and T. Crook. 2009. Why does cytotoxic chemotherapy cure only some cancers? *Nat Clin Pract Oncol* 6 (1):43-52.

Sporn, M. B. 1996. The war on cancer. *Lancet* 347 (9012): 1377-1381.

Sugarbaker, P. H., W. Yu, and Y. Yonemura. 2003. Gastrectomy, peritoneotomy, and perioperative intraperitoneal chemotherapy: the evolution of treatment strategies for advanced gastric cancer. *Semin Surg Oncol* 21 (4):233-248.

Tan, D. S., R. Agarwal, and S. B. Kaye. 2006. Mechanisms of transcoelomic metastasis in ovarian cancer. *Lancet Oncol* 7 (11):925-934.

Tanos, B., and E. Rodriguez-Boulan. 2008. The epithelial polarity program: machineries involved and their hijacking by cancer. *Oncogene* 27 (55):6939-6957.

Todaro, G. J., G. K. Lazar, and H. Green. 1965. Initiation of Cell Division in a Contact-Inhibited Mammalian Cell Line. *Journal of Cellular and Comparative Physiology* 66 (3P1): 325-&.

Vermeer, P. D., L. A. Einwalter, T. O. Moninger, T. Rokhlina, J. A. Kern, J. Zabner, and M. J. Welsh. 2003. Segregation of receptor and ligand regulates activation of epithelial growth factor receptor. *Nature* 422 (6929):322-326.

Wang, F., V. M. Weaver, O. W. Petersen, C. A. Larabell, S. Dedhar, P. Briand, R. Lupu, and M. J. Bissell. 1998. Reciprocal interactions between beta 1-integrin and epidermal growth factor receptor in three-dimensional basement membrane breast cultures: a different perspective in epithelial biology. *Proc Natl Acad Sci USA* 95 (25):14821-14826.

Yamada, K. M., and E. Cukierman. 2007. Modeling tissue morphogenesis and cancer in 3D. *Cell* 130 (4):601-610.

Yarrow, J. C., Z. E. Perlman, N. J. Westwood, and T. J. Mitchison. 2004. A high-throughput cell migration assay using scratch wound healing, a comparison of image-based readout methods. *BMC Biotechnol* 4:21.

Zahm, J. M., H. Kaplan, A. L. Herard, F. Doriot, D. Pierrot, P. Somelette, and E. Puchelle. 1997. Cell migration and proliferation during the in vitro wound repair of the respiratory epithelium. *Cell Motil Cytoskeleton* 37 (1):33-43.

Other Embodiments

It is to be understood that while methods and devices have been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method to detect motility of cells, the method comprising:

isolating a cell population from a tissue sample obtained from a patient, the cell population comprising isolated cells;

allowing a cell from the cell population to enter an opening in a microcapillary channel under conditions effective to permit a single cell from the cell population to enter the microcapillary channel, the microcapillary channel opening having a cross sectional area that is smaller than a maximum cell diameter of the cell from the cell population outside the microcapillary channel; and detecting the presence of a motile cell in the cell population by observing a unidirectional movement of the cell away from the opening in the microcapillary channel in the absence of a chemical gradient.

2. The method of claim 1, wherein the cell population comprises an isolated cancer cell population, the cell comprises a cancer cell, and allowing a cell to enter the opening in the microcapillary channel comprises:

forming a cell suspension comprising the isolated cancer cell population; and contacting the cell suspension to the opening in the microcapillary channel.

3. The method of claim 2, wherein the unidirectional movement of the cancer cell along a length of the microcapillary channel away from the opening continues for at least six minutes.

4. The method of claim 2, wherein the unidirectional movement of the cancer cell along a length of the microcapillary channel away from the opening occurs in the absence of serum.

5. The method of claim 2, wherein the method further comprises contacting an interior surface of the microcapillary channel with an extracellular matrix protein prior to allowing the cancer cell from the cancer cell population to enter the opening in the microcapillary channel.

6. The method of claim 5, wherein the extracellular matrix protein comprises collagen.

7. The method of claim 1, wherein a length of the microcapillary channel includes a bend or loop.

8. The method of claim 7, wherein a cross-sectional area of an interior of the microcapillary channel is substantially constant along the length of the microcapillary channel.

9. The method of claim 8, wherein the microcapillary channel has a ratio of the cross-sectional area of the interior of the microcapillary channel and the length of the microcapillary channel of less than about 1.0 micrometer.

10. The method of claim 9, wherein the ratio of the cross-sectional area of the interior of the microcapillary channel and the length of the microcapillary channel is less than about 0.5 micrometer.

11. The method of claim 2, wherein contacting the cancer cell to the opening of the microcapillary channel comprises introducing a solution comprising the cancer cell into a reservoir in fluid flow communication with the opening of the microcapillary channel.

12. The method of claim 2, wherein the cancer cell population is obtained from a subject at a location selected from the group consisting of a prostate, a breast, a lung, a colon and a brain.

13. The method of claim 2, wherein the unidirectional movement of the cancer cell away from the opening in the microcapillary channel occurs at a rate of at least about 7.5 micrometers per hour.

14. The method of claim 2, further comprising:

(a) contacting the cancer cell in the isolated cancer cell population with a chemical agent; and (b) determining whether the cancer cell is a motile cancer cell after contacting the chemical agent.

15. A method of measuring cell motility of a cell along a length of a microcapillary channel, the method comprising:

(a) obtaining an isolated cell having a maximum diameter;

(b) contacting the isolated cell to an opening in a microcapillary channel under conditions effective to permit the isolated cell to enter the microcapillary channel, the microcapillary channel opening having a cross sectional area along the length of the microcapillary channel that is smaller than the maximum diameter of the cell outside the microcapillary channel; and (c) detecting movement of the isolated cell within the microcapillary channel in an absence of a chemical gradient along the length of the microcapillary channel away from the opening to measure the cell motility of the isolated cell within the microcapillary channel.

16. The method of claim 15, wherein the cell is a cancer cell, a stem cell, or a fibroblast.

17. A method to detect motility of cells, the method comprising:

isolating a cell population from a tissue sample obtained from a patient, wherein said isolated cell population comprises cancer cells;

forming a cell suspension comprising said cells;

allowing a cell from said suspension to enter an opening in a microcapillary channel by contacting the cell suspension with said opening under conditions effective to permit a single cell from said population to enter the microcapillary channel;

wherein the microcapillary channel opening has a cross sectional area that is smaller than a maximum cell diameter of said cell from the cell population outside the microcapillary channel;

and detecting the presence of a motile cell by observing a unidirectional movement of the cell away from the opening in the microcapillary channel in the absence of a chemoattractant gradient.

18. A method of measuring cell motility of a cell along a length of a microcapillary channel, the method comprising:

(a) obtaining an isolated cell having a maximum diameter;

(b) contacting the isolated cell to an opening in a microcapillary channel under conditions effective to permit the isolated cell to enter the microcapillary channel, the microcapillary channel opening having a cross sectional area along the length of the microcapillary channel that is smaller than the maximum diameter of the cell outside the microcapillary channel; and (c) detecting movement of the isolated cell within the microcapillary channel in an absence of a chemical chemoattractant gradient along the length of the microcapillary channel away from the opening to measure the cell motility of the isolated cell within the microcapillary channel, wherein the cell is a cancer cell, a stem cell, or a fibroblast.

* * * * *